United States Patent [19]

Shapland et al.

[11] Patent Number: 5,807,306

[45] Date of Patent: Sep. 15, 1998

[54] POLYMER MATRIX DRUG DELIVERY APPARATUS

[75] Inventors: J. Edward Shapland, Shoreview, Minn.; Keith R. Hildelbrand, Houlton, Wis.; Joel R. Racchini, Edina, Minn.; Jin Shimada, Falcon Heights, Minn.; Mark B. Knudson, Shoreview, Minn.

[73] Assignee: CorTrak Medical, Inc., Roseville, Minn.

[21] Appl. No.: 291,394

[22] Filed: Aug. 16, 1994

Related U.S. Application Data

[63] Continuation-in-part of Ser. No. 203,811, Mar. 1, 1994, abandoned, and a continuation-in-part of Ser. No. 973,263, Nov. 9, 1992, abandoned.

[51] Int. Cl.$^6$ ........................................................ A61N 1/30
[52] U.S. Cl. ................................................ 604/21; 604/96
[58] Field of Search .............................. 604/20–22, 49, 604/52, 53, 96, 101, 265; 606/192, 194

[56] References Cited

U.S. PATENT DOCUMENTS

| | | |
|---|---|---|
| 430,928 | 6/1890 | Doty . |
| 578,611 | 3/1897 | Rively . |
| 725,731 | 4/1903 | Linn . |
| 873,021 | 12/1907 | Cool . |
| 2,123,980 | 7/1938 | Warwick . |
| 2,499,045 | 2/1950 | Walker et al. . |
| 2,649,854 | 8/1953 | Salm . |
| 2,696,209 | 12/1954 | Varaney . |
| 2,848,998 | 8/1958 | Bryan . |
| 3,173,418 | 3/1965 | Baran . |
| 3,542,014 | 11/1970 | Peronneau . |
| 3,593,713 | 7/1971 | Bogoff et al. . |
| 3,826,828 | 7/1974 | Morel . |

(List continued on next page.)

FOREIGN PATENT DOCUMENTS

| | | |
|---|---|---|
| 299 698 | 1/1989 | European Pat. Off. . |
| 0 372 088 | 6/1990 | European Pat. Off. . |
| 0 399 712 | 11/1990 | European Pat. Off. . |
| 0 438 078 | 7/1991 | European Pat. Off. . |
| 147 314 | 4/1981 | German Dem. Rep. . |
| 39 15 636 | 4/1990 | Germany . |
| 49-132888 | 12/1974 | Japan . |
| 588 870 | 6/1977 | Switzerland . |
| 1003-853-A | 3/1983 | U.S.S.R. . |
| 1 069 827 | 1/1984 | U.S.S.R. . |

(List continued on next page.)

OTHER PUBLICATIONS

*Iontophoretic Transmyocardial Drug Delivery, A Novel Approach to Antiarrhythmic Drug Therapy*; Boaz Avitall et al.; Aug. 17, 1990; revised Dec. 10, 1991; pp. 1582–1593.
*Epicardial Iontophoretic Delivery of Antiarrhythmic Agents*; Vinod Labhasetwar et al.; Proceed. Intern. Symp. Control. Rel. Bioact. Mater., 20 (1993), Controlled Release Society, Inc.
T. Okada et al., "Local Anticoagulation Without Systemic Effect Using A Polymer Heparin Delivery System,"*Stroke*, vol. 19, No. 12, Dec. 1988, pp. 1470–1476.
D. Skaven et al., "Phonophoresis," *International Journal of Pharmaceutics*, 20 (1984), pp. 235–245.
Antich, "Phonophoresis: The Principles of the Ultrasonic Driving Force and Efficacy in Treatment of Common Orthopaedic Diagnoses", *Journal of Orthopaedic and Sports Physical Therapy, 4(2)*, 99–102 (1982).
*BBI Newsletter, 13(5)*, 85–91 (1990).

(List continued on next page.)

*Primary Examiner*—Corrine M. McDermott
*Attorney, Agent, or Firm*—Merchant, Gould, Smith, Edell, Welter & Schmidt, P.A.

[57] ABSTRACT

A drug delivery apparatus and method for delivering a drug locally to internal body tissue using a catheter device including a polymer matrix containing a drug. The drug is actively transported from the polymer matrix to the internal body tissue using iontophoresis or phonophoresis. In addition, the polymer matrix can be expanded to promote intimate contact with the walls of a passageway or vessel.

10 Claims, 9 Drawing Sheets

U.S. PATENT DOCUMENTS

| | | |
|---|---|---|
| 3,865,108 | 2/1975 | Hartop . |
| 3,993,058 | 11/1976 | Hoff . |
| 4,126,134 | 11/1978 | Bolduc et al. . |
| 4,137,906 | 2/1979 | Akiyama et al. . |
| 4,176,664 | 12/1979 | Kalish . |
| 4,202,346 | 5/1980 | Granier . |
| 4,280,503 | 7/1981 | Ackerman . |
| 4,323,071 | 4/1982 | Simpson et al. . |
| 4,332,243 | 6/1982 | Gutnick . |
| 4,338,942 | 7/1982 | Fogarty . |
| 4,364,392 | 12/1982 | Strother et al. . |
| 4,365,631 | 12/1982 | Kline . |
| 4,383,529 | 5/1983 | Webster . |
| 4,403,612 | 9/1983 | Fogarty . |
| 4,411,648 | 10/1983 | Davis et al. . |
| 4,415,548 | 11/1983 | Reddy . |
| 4,416,274 | 11/1983 | Jacobsen et al. . |
| 4,417,576 | 11/1983 | Baran . |
| 4,456,012 | 6/1984 | Lattin . |
| 4,509,523 | 4/1985 | Pevsner . |
| 4,551,132 | 11/1985 | Pasztor et al. . |
| 4,572,186 | 2/1986 | Gould et al. . |
| 4,573,966 | 3/1986 | Weikl et al. . |
| 4,582,181 | 4/1986 | Samson . |
| 4,606,337 | 8/1986 | Zummermann et al. . |
| 4,608,984 | 9/1986 | Fogarty . |
| 4,610,662 | 9/1986 | Weikl et al. . |
| 4,636,195 | 1/1987 | Wolinsky . |
| 4,663,358 | 5/1987 | Hyon et al. . |
| 4,689,041 | 8/1987 | Corday . |
| 4,693,704 | 9/1987 | Ogita . |
| 4,698,058 | 10/1987 | Greenfeld et al. . |
| 4,705,507 | 11/1987 | Boyles . |
| 4,714,460 | 12/1987 | Calderon . |
| 4,733,665 | 3/1988 | Palmaz . |
| 4,744,366 | 5/1988 | Jang . |
| 4,767,402 | 8/1988 | Kost et al. . |
| 4,776,337 | 10/1988 | Palmaz . |
| 4,787,888 | 11/1988 | Fox . |
| 4,800,882 | 1/1989 | Gianturco . |
| 4,819,637 | 4/1989 | Dormandy, Jr. et al. . |
| 4,819,751 | 4/1989 | Shimada et al. . |
| 4,824,436 | 4/1989 | Wolinsky . |
| 4,829,991 | 5/1989 | Boeck . |
| 4,832,688 | 5/1989 | Sagae et al. . |
| 4,866,050 | 9/1989 | Ben-Amoz . |
| 4,867,968 | 9/1989 | Allen . |
| 4,869,241 | 9/1989 | Friedmann . |
| 4,879,135 | 11/1989 | Greco et al. . |
| 4,948,587 | 8/1990 | Kost et al. . |
| 5,000,734 | 3/1991 | Boussignac et al. . |
| 5,007,897 | 4/1991 | Kalb et al. . |
| 5,041,093 | 8/1991 | Chu . |
| 5,041,107 | 8/1991 | Heil, Jr. ............................ 604/891.1 |
| 5,047,028 | 9/1991 | Qian . |
| 5,049,132 | 9/1991 | Shaffer et al. . |
| 5,087,243 | 2/1992 | Avital . |
| 5,087,244 | 2/1992 | Wolinsky et al. . |
| 5,092,841 | 3/1992 | Spears ...................................... 604/96 |
| 5,102,402 | 4/1992 | Dror et al. . |
| 5,222,936 | 6/1993 | Stephen et al. . |
| 5,232,441 | 8/1993 | Stephen et al. . |
| 5,232,444 | 8/1993 | Just et al. . |
| 5,236,413 | 8/1993 | Feiring ...................................... 604/21 |
| 5,279,594 | 1/1994 | Jackson . |
| 5,286,254 | 2/1994 | Shapland et al. . |
| 5,304,121 | 4/1994 | Sahatjian ................................. 604/53 |

FOREIGN PATENT DOCUMENTS

| | | |
|---|---|---|
| 1069-826-A | 1/1984 | U.S.S.R. . |
| 1069826 | 1/1984 | U.S.S.R. . |
| 1 146 057 | 3/1985 | U.S.S.R. . |
| 1 410 973 | 7/1988 | U.S.S.R. . |
| 81 03733 | 12/1981 | WIPO . |
| 83 04182 | 12/1983 | WIPO . |
| WO 89/01794 | 3/1989 | WIPO . |
| WO 89/12478 | 6/1989 | WIPO . |
| WO 91/16945 | 11/1991 | WIPO . |
| WO 91/19529 | 12/1991 | WIPO . |
| 92 15363 | 9/1992 | WIPO . |
| 92 12654 | 10/1992 | WIPO . |
| 92 19321 | 11/1992 | WIPO . |
| 94 07413 | 4/1994 | WIPO . |

OTHER PUBLICATIONS

Brand, "Preventing Reocclusion After MI Reperfusion Therapy", *Cardio,* November, 48–56 (1989).

Ellman et al., "Renal Ablation with Absolute Ethanol, Mechanism of Action", *Investigative Radiology, 19(5),* 416–423 (1984).

Goldman et al., "Influence of Pressure on Permeability of Normal and Diseased Muscular Arteries to Horseradish Peroxidase, A New Catheter Approach", *Atherosclerosis,* 65 215–225 (1987).

Jorgensen et al., *The Lancet,* May 20, 1106–1108 (1989).

Klimberg et al., "Absolute Ethanol Renal Angioinfarction for Control of Hypertension", *Urology, 33(2),* 153–158 (1989).

Layer et al., "Early Aneurysmal Degeneration of Human Umbilical Vein Bypass Grafts", *Br. J. Surg.,* 71709–710 (1984).

Okada et al., Local Anticoagulation Without Systemic Effect Using a Polymer Heparin Delivery System, *Stroke, 19(12),* 1470–1476, (1988).

Okada et al., Localized Release of Perivascular Heparin Inhibits Intimal Proliferation After Endothelial Injury Without Systemic Anticagulation, *Neurosurgery, 25(6),* 892–898 (1989).

Sheehan and Hrapchak, "Fixation", *Theory and Practice of Histotechnology,* Ch. 2, 40–50 (1984).

Skauen et al., "Phonophresis", *International Journal of Pharmaceutics, 20* 235–245 (1984).

Wolinsky et al., Use of a Perforated Balloon Catheter to Deliver Concentrated Heparin into the Wall of the Normal Canine Artery, *JACC, 15(2),* 475–481 (1990).

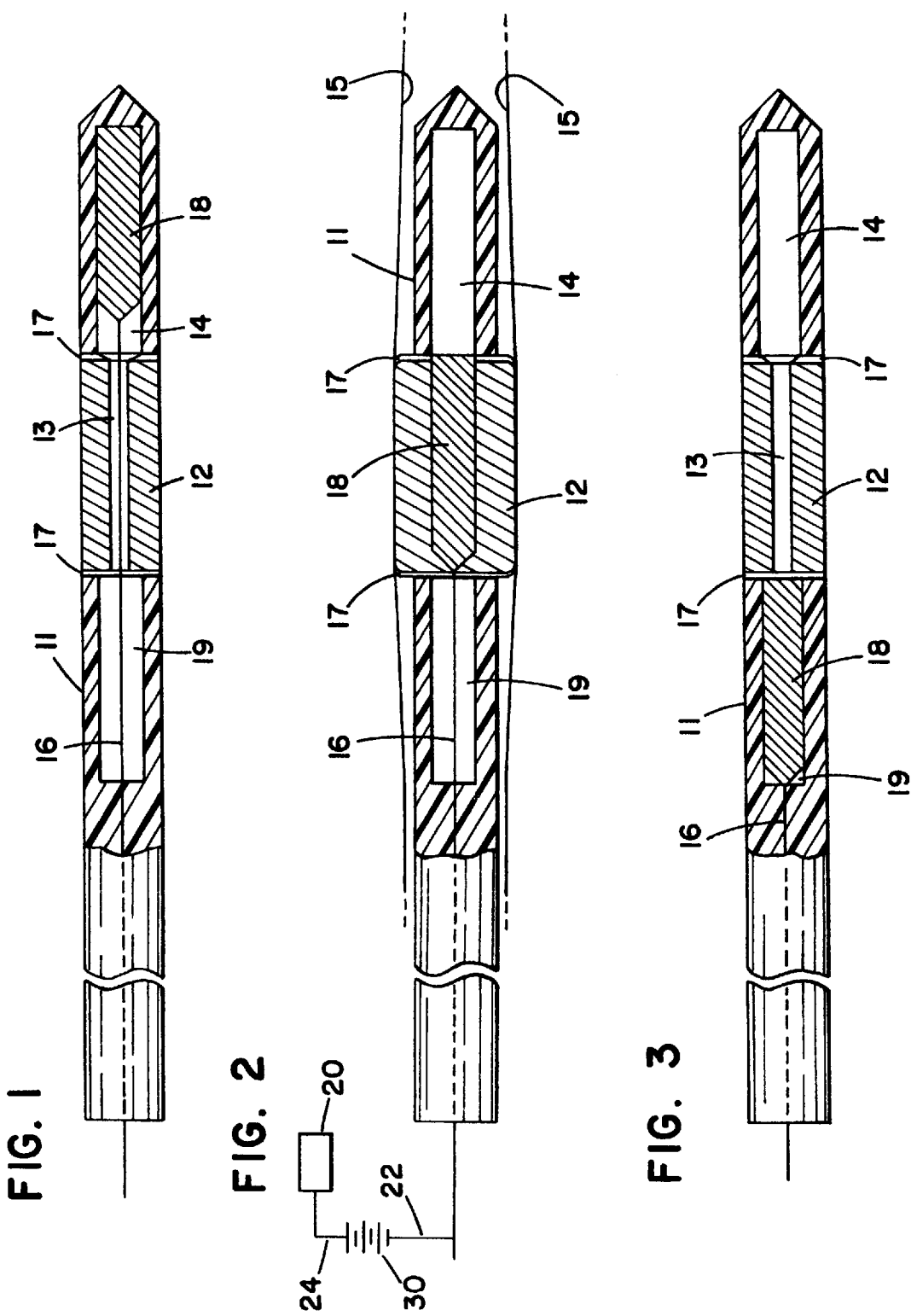

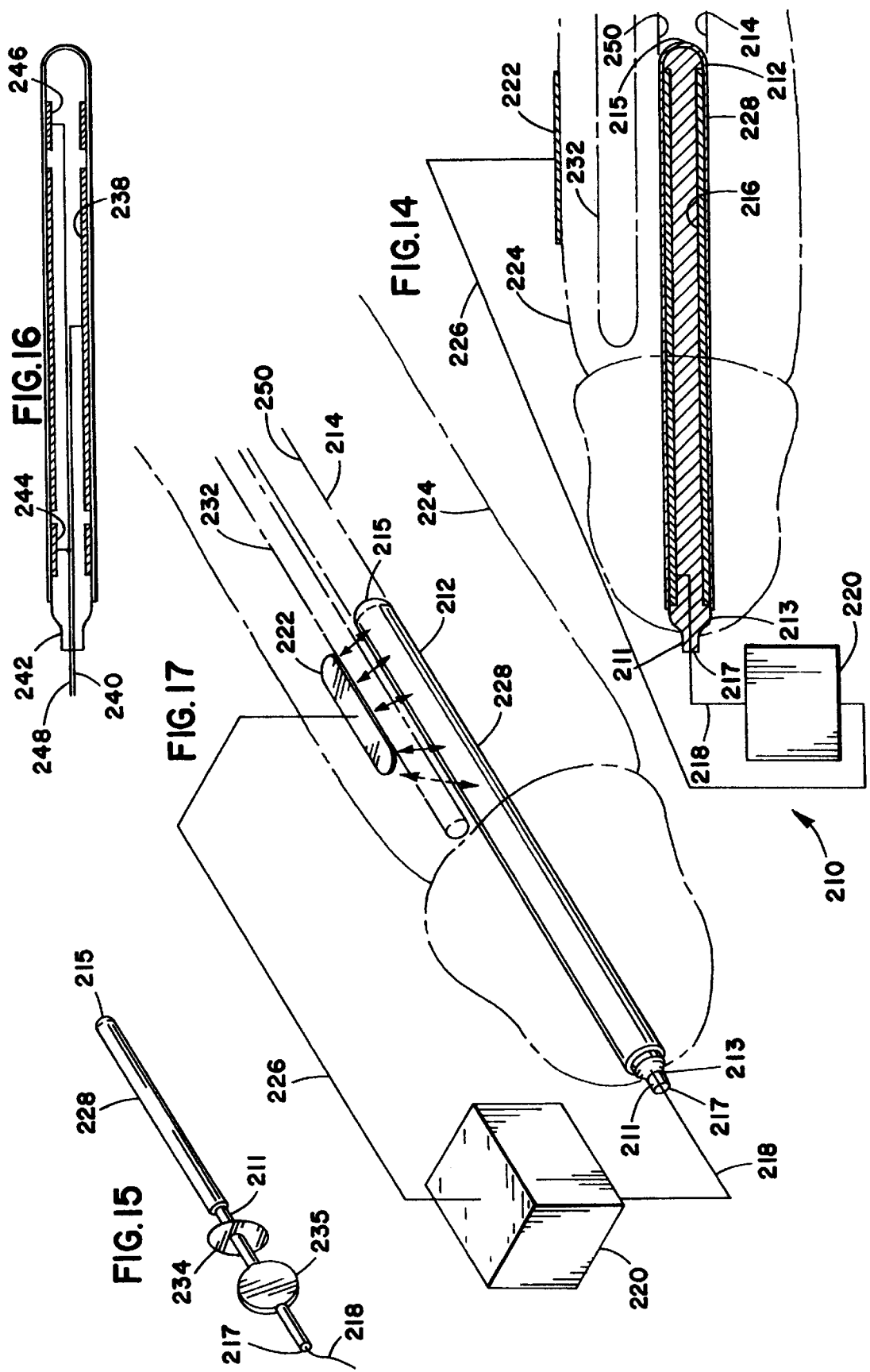

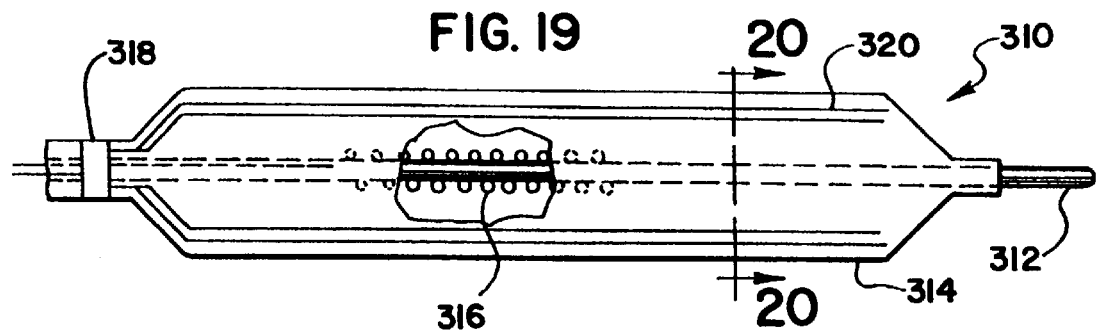
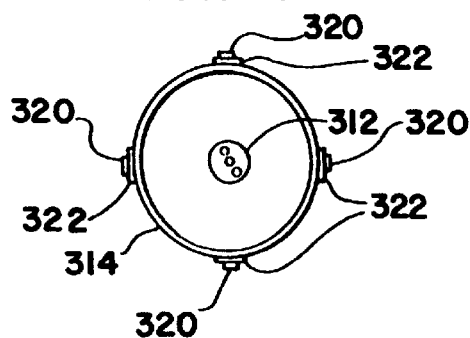
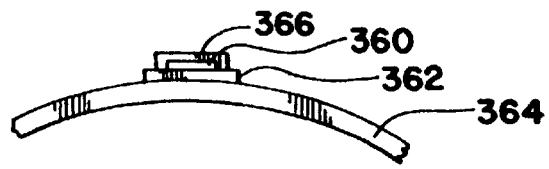
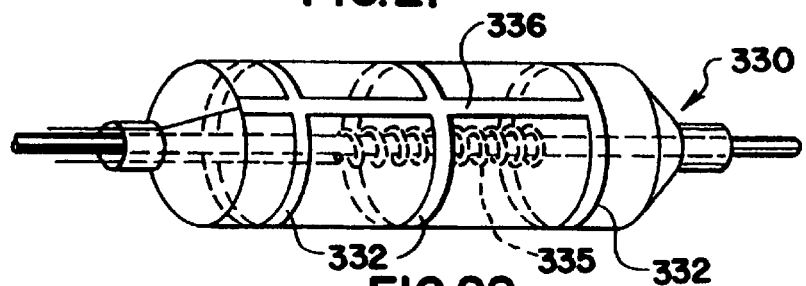
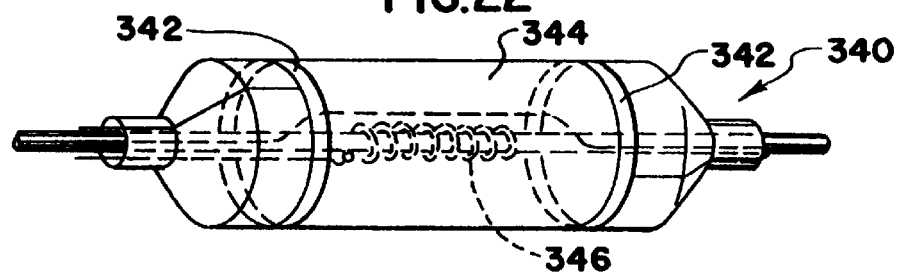
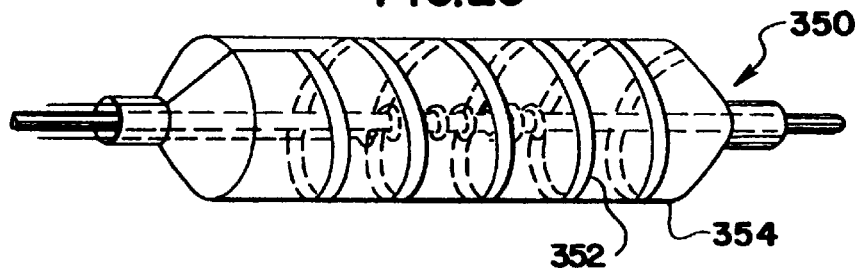

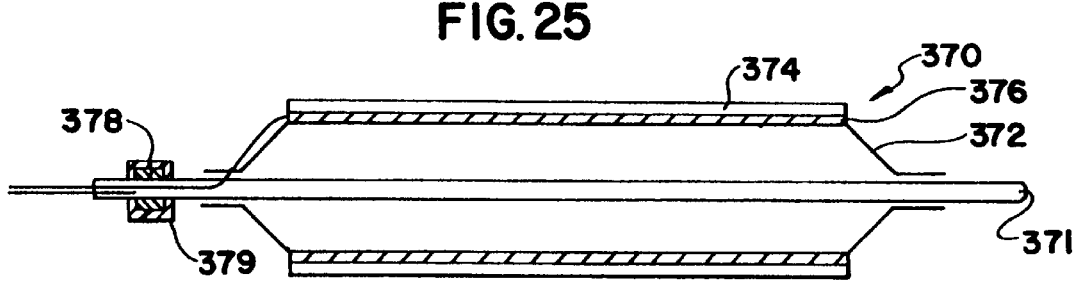
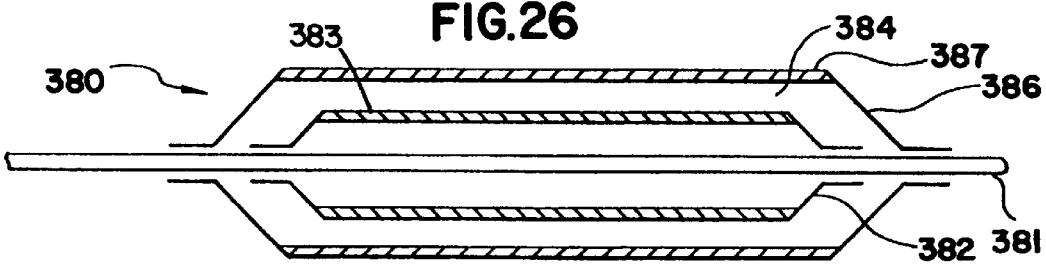
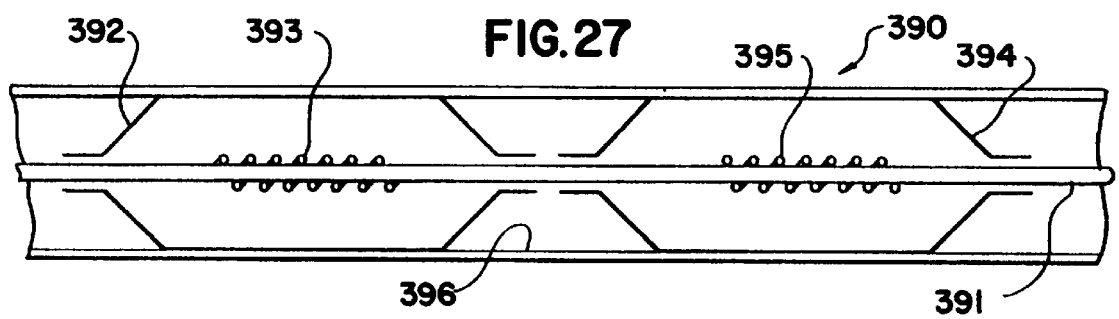
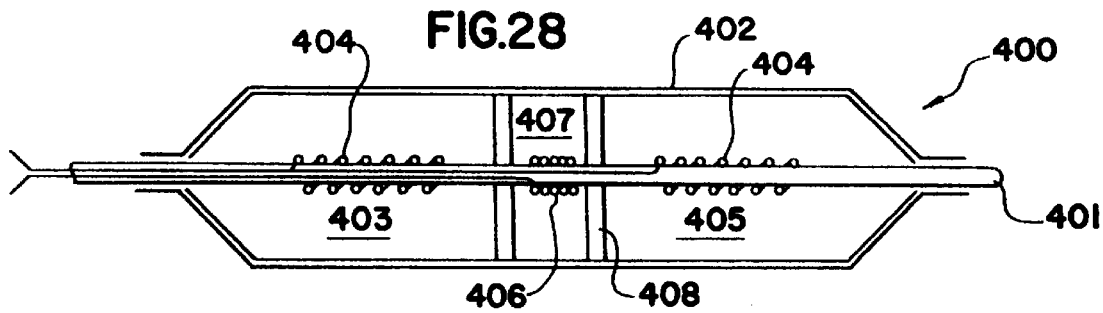
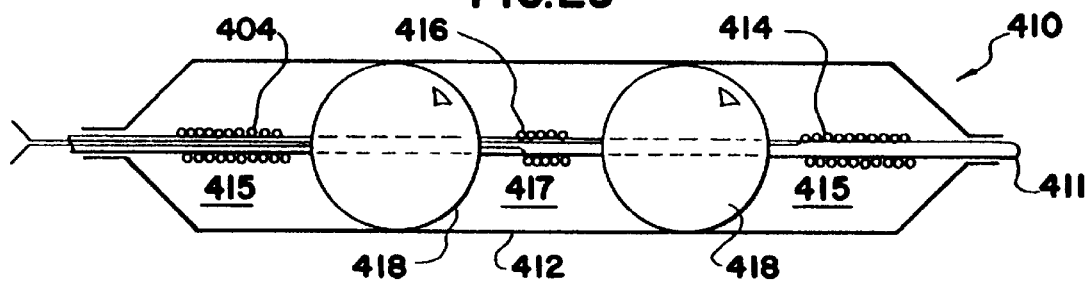

POLYMER MATRIX DRUG DELIVERY APPARATUS

REFERENCE TO CO-PENDING APPLICATIONS

This application is a continuation-in-part of U.S. patent application Ser. No. 08/203,811, filed Mar. 1, 1994 now abandoned and entitled MULTIPLE ELECTRODE DRUG DELIVERY APPARATUS AND METHOD. This application is also a continuation-in-part of U.S. patent application Ser. No. 07/973,263, filed Nov. 9, 1992 now abandoned and entitled POLYMER MATRIX DRUG DELIVERY APPARATUS AND METHOD.

TECHNICAL FIELD

The present invention relates to a drug delivery apparatus and method for selectively and locally delivering a drug to internal body tissue. More particularly, the present invention relates to a catheter device including a polymer matrix containing a drug and transport means for actively transporting the drug from the catheter device to the internal body tissue.

BACKGROUND

Many techniques currently exist for delivering drugs or other medicaments to body tissue. These include topical or transcutaneous administration where the drug is passively absorbed, or caused to pass, into or across the skin or other surface tissue; oral administration; injection directly into body tissue such as through an intramuscular injection or the like; and intravenous administration, which involves introducing a selected drug directly into the blood stream.

Transcutaneous drug delivery systems are usually limited to external administration of a drug through the patient's skin or other surface tissue. Delivery through the skin is inefficient because some of the drug may be absorbed by healthy tissue before it reaches the diseased or damaged area. Additionally, some of the drug may be picked up by dermal capillaries and carried beyond the diseased or damaged area. Thus, transcutaneous drug delivery systems are not always appropriate for the localized treatment of internal body tissue, especially if the required drug is toxic or burdensomely expensive.

Oral administration, injection, and intravenous administration are systemic. In other words, drug is delivered throughout the body by the blood stream. This type of drug delivery system has many shortcomings. The reason is that systemic delivery systems fail to concentrate the drug in the local area where it is required. As a result, a higher quantity of drug is needed in order to get the proper dosage to the area that needs treatment. The resulting high quantity of drug adds extra expense to the medical treatment and can cause harmful side effects.

Thus, there is a need for a localized drug delivery system that allows the use of therapeutic agents including those that were previously considered too toxic or non-specific to administer systemically. The advantages of localized internal drug delivery over systemic administration are known and described in, for example, U.S. Pat. No. 5,286,254, which is entitled Drug Delivery Apparatus and Method. That application also discusses some situations in which localized internal drug delivery is especially advantageous, including the treatment of a dilated vessel to reduce restenosis following percutaneous transluminal coronary angioplasty (PTCA) and the delivery of drugs to tumors.

In PTCA, catheters are inserted into the cardiovascular system under local anesthesia and an expandable balloon portion is then inflated to compress the atherosclerosis and dilate the lumen of the artery. Despite the general success of such PTCA procedures, high restenosis rates (reported to be as high as 47%) is a major problem. People have tried various techniques to treat stenosed vessels including the use of lasers, application of heat and the use of intravascular stents. However, many of these are still under investigation with mixed results, while others are not generally successful. The ability to administer a drug locally to the dilated portion of the artery in PTCA procedures, without significantly affecting other tissues, would greatly enhance the ability to address the restenosis problem.

In the treatment of tumors, an objective is to administer the cancer drug so that it localizes, as much as possible, in the tumor itself. Such drugs are commonly administered systemically through the blood stream. Various means are then utilized for causing the drug to localize in the cancer tumor. Nevertheless, significant portions of the drug still circulate through the blood stream, thereby affecting non-cancerous tissue, producing undesirable side effects, and limiting the dosages of the drug that can be safely administered.

Researches have developed catheter-based drug delivery systems to accomplish the above procedures. For example, double-balloon catheters are used to administer agents to the area confined by the balloons in a vessel or other body passageway. That system, however, has a disadvantage because a portion of the drug may pass into communicating vessels between the balloons and be carried beyond the diseased or damaged area. Another example is perforated balloons that are used to deliver pressurized drug solutions across a porous balloon wall and directly into a hollow organ.

Although the catheter-based local drug delivery systems are somewhat effective, they are typically designed to deliver therapeutic agents in solution. This limitation has several disadvantages.

First, the desired therapeutic agent must be readily soluble in an appropriate solvent. However, many drugs are not easily solubilized in aqueous-based solvents.

Second, the catheters are equipped with conduits to introduce and possibly evacuate the liquid solution, as well as a terminal drug reservoir. Such devices typically use inflatable balloons that either act as drug reservoirs or restrict drug movement to a specific segment of the vessel or hollow organ. In addition to the conduits needed to introduce and evacuate the liquid drug solution, one or more conduits are also provided to inflate and deflate the catheter balloon. Multiple conduits increase the complexity, cost, and profile of the catheter. Thus, there are only limited applications for which it can be used.

Third, because the catheter delivers fluids, there is a risk of leakage from a defective or damaged conduit or balloon. Leakage can result in a serious overdosage or simply result in the waste of a valuable medication that is targeted for local delivery.

Fourth, a physician or other medical personal must prepare the liquid drug solution and introduce it into the catheter. Such procedures add time, complication, and expense to the use of these devices and are thus more likely to result in the administration of inaccurate dosages.

U.S. Pat. No. 5,102,402 to Dror et al. discloses the use of drugs contained in micro-capsules located on the outer surface of a balloon catheter. The capsules are ruptured using sonic energy. Upon rupturing, the capsules deliver the drug internally. This patent does not disclose the use of phonophoresis to actively transport the drugs into the surrounding tissue. Instead, the drug is delivered through passive diffusion, thereby limiting its penetration.

Both U.S. Pat. No. 1,069,826 to Zaporo and U.S. Pat. No. 5,236,413 to Feiring disclose a catheter with a balloon having discrete holes or perforations. The interior of the balloon contains a drug for transport to the adjacent tissue. During delivery, the drug passes from the interior of the balloon, through the holes in the balloon, and into the adjacent tissue. The balloon material in the Zaporo and Feiring patents do not hold the drug itself, but merely acts as a barrier. Thus, the Zaporo and Feiring patents do not disclose drug delivery devices in which the drug is held within a polymer matrix that covers the surface of the balloon or catheter.

In addition to the treatment of maladies such as PTCA and tumors, localized drug delivery is also advantageous in the treatment of erectile dysfunction. A dysfunction can result from either physiological or psychological factors. If a physiological problem, impotence is generally characterized by blood flow to and from the penis remaining in balance. This balance prevents the retention of a sufficient amount blood to cause rigid dilation of the corpora cavernosa and spongiosa.

Common treatments for erectile dysfunctions include injecting a drug into the corpora of the penis with a syringe or other needle-type device, surgically inserting a prothesis or other mechanical apparatus, and delivering a drug into the urethra and waiting for the drug to be absorbed. Each of these methods include unsatisfactory features such as pain or excessive delay in delivery of the drug.

A method for treating erectile dysfunctions is shown in U.S. Pat. No. 5,242,391 to Place et al. In that patent, a dose of an agent is carried on an applicator. The applicator is inserted into the urethra and the dose is applied through transurethral administration. This device has several shortcomings. For instance, it relies on passive diffusion of the drugs. As a result, the drug's penetration into tissue is both limited and slow. The patent suggests that the treatment takes as long as 10 to 15 minutes before it is effective.

Transportation of a drug using a localized drug delivery system is enhanced through means such as iontophoresis. The Detailed Description defines iontophoresis and discusses it in greater detail. Additionally, U.S. Pat. No. 5,286,254, which is discussed above, discusses the use of iontophoresis to enhance localized drug delivery.

Devices that provide a plurality of electrodes internal within a patient's body are known, although not for percutaneously administered internal drug delivery purposes. Examples of such devices include electrodes used in pacing devices and transvenous leads for implantable defibrillators. Those devices are primarily provided to control electrical activity related to the heart.

U.S. Pat. No. 5,087,234 to Avitall and the associated article by Avitall et al. titled "Iontophoretic Transmyocardial Drug Delivery", *Circulation*, pp. 1582–1593, Vol. 85 (1992) discuss the delivery of antiarrhythmic agents locally to arrhythmogenic tissue through the use of a long-term implantable reservoir attached to the tissue. The apparatus and methods discussed focus on the delivery of a drug from an implantable reservoir that is surgically attached. This procedure requires a sternotomy to expose the heart. The antiarrhythmic agents are then delivered from the reservoir using iontophoresis in which current is pulsed in conjunction with the intrinsic heartbeat.

One disadvantage of the methods and apparatuses discussed by Avitall et al. is the requirement of surgically opening the patient's chest cavity in order to place the reservoir. Such procedures dramatically increase the morbidity of localized internal drug delivery, especially compared to methods of percutaneously introducing an apparatus that provides localized internal drug delivery.

The catheter described in U.S. Pat. No. 5,236,413 to Feiring utilizes iontophoresis to assist localized internal drug delivery. The disclosure of the Feiring patent is limited to the use of one electrode within a drug delivery chamber and a second external electrode located on the surface of the patient's skin. Furthermore, additional embodiments of the Feiring apparatus include a plurality of external electrodes located about the patient's torso in an attempt to control the electric field and thus the distribution of the drug. However, the actual ability of external patch electrodes to control the electric field in conjunction with an internal electrode is questionable due to the high impedance and capacitance associated with skin.

Devices and methods that employ an electrode located within the patient's body and one or more external electrodes suffer from a number of disadvantages. Specifically, devices employing external electrodes require higher voltage levels to overcome the high impedance of a patient's skin. That higher voltage level can, in some instances, increase the risk of inducing cardiac arrhythmias and other unwanted side effects such as muscle stimulation. Furthermore, the higher voltage levels required to overcome the high impedance of the skin can adversely affect the patient's skin if current densities underneath the patch electrode exceed an allowable level.

In addition, the high impedance and high capacitance of the skin can adversely affect the integrity of waveforms that are used to accomplish iontophoretic drug delivery. This result is especially true if high frequency waveforms are used. Attempts to overcome the impedance and capacitance, such as further increasing voltage, can create an even higher risk of inducing cardiac arrhythmias.

Accordingly, there is a need in the art for a method and apparatus for active delivery of a drug to internal body tissue that is more precise, efficient, and simple. There is a further need for such a system and method for the localized treatment of internal body tissues to limit restenosis following PTCA, to treat cancerous tumors or the like, or to treat various other medical situations including erectile dysfunction. Even further, there is a need for an apparatus for percutaneously introducing and delivering a drug selectively and locally to internal body tissue that employs electric current provided by a plurality of internal electrodes to enhance the delivery of drugs.

SUMMARY

In accordance with the present invention, an apparatus and method is provided for active delivery of a drug or combination of drugs selectively and locally to internal solid body tissue using a polymer matrix incorporated into a catheter-based delivery system. The drug delivery apparatus has a catheter for insertion into an internal target area of a body. A polymer matrix is operably connected to the catheter, wherein the polymer matrix embodies the drug. The apparatus also includes transport means for actively transporting the drug from the polymer matrix to the internal solid body tissue.

The method of delivering a drug to internal solid body tissue includes the initial step of inserting a distal end of the catheter into the body so that it is proximate the internal solid body tissue. The catheter includes a polymer matrix proximate the distal end, and the polymer matrix embodies the drug. The drug is then transported from the polymer matrix to the internal solid body tissue using transport means that is proximate the distal end of the catheter.

An alternative embodiment of a method of delivering drugs to a local area of internal body tissue includes the step of percutaneously introducing a catheter that has an elongated body. The catheter further includes a distal end, a proximal end, drug delivery means for localized delivery of the drug to internal body tissue of a patient. The drug delivery means are located proximate the distal end of the elongated body, and a supply electrode is located within the drug delivery means. The next step is locating a return electrode internally within the body of the patient. Electric current/potential is then provided between the supply electrode and the return electrode, thereby causing delivery of the drug from the drug delivery means to the internal body tissue. An additional catheter embodiment employs a supply electrode located within the drug delivery means and a return electrodes internally within the body of the patient.

A method of relieving erectile impotence in a human male includes selecting a treatment tool having an insert end sized for removable insertion into an urethra of a penis. The tool has an impotence therapeutic drug contained on the insert end. The therapeutic drug is dischargeable for transurethral phoretic application upon activation of the tool. Next, the insert end is inserted into the urethra. The tool is activated, thereby causing phoretical application of the drug transurethrally across the urethra. The insert end is then removed from the urethra.

DESCRIPTION OF THE DRAWINGS

FIG. 1 is a fragmentary view, partially in section, of a first embodiment of the drug delivery apparatus of the present invention in the form of a catheter with a polymer matrix and transport means before expansion.

FIG. 2 is a fragmentary view, partially in section, of the drug delivery apparatus of FIG. 1 with the transport means located within and expanding the polymer matrix.

FIG. 3 is a fragmentary view, partially in section, of the apparatus of FIG. 1, after removal of the transport means from the polymer matrix.

FIG. 14 is a cross-sectional view of a catheter designed for treating erectile dysfunction.

FIG. 15 is a perspective view of the catheter shown in FIG. 14.

FIG. 16 is a perspective view of an alternative embodiment of the catheter shown in FIG. 14.

FIG. 17 is a cross-sectional view of another alternative embodiment of the catheter shown in FIG. 14.

FIG. 19 is a partial view in cross-section of one embodiment of a drug delivery apparatus according to the present invention.

FIG. 20 is a cross-sectional view of the apparatus of FIG. 19 along line 2—2.

FIG. 21 is a perspective view of an alternate embodiment of a catheter according to the present invention incorporating conductive portions on the outer surface of a catheter.

FIG. 22 is a perspective view of an alternate embodiment of an apparatus according to the present invention incorporating ring electrodes on the surface of a catheter.

FIG. 23 is a perspective view of an alternate embodiment of a catheter according to the present invention incorporating an electrode on the surface of the catheter deposited in a helical pattern.

FIG. 24 is a partial view in cross-section of an alternate embodiment of a drug delivery apparatus according to the present invention incorporating an insulating material between a return electrode and a balloon.

FIG. 25 is a partial view in cross-section of an alternate embodiment of a drug delivery apparatus according to the present invention incorporating a polymer matrix material deposited on a balloon over an electrically conductive coating on the outer surface of the balloon.

FIG. 26 is partial view in cross-section of an alternate embodiment of a drug delivery apparatus according to the present invention incorporating dual concentric balloons, with electrodes mounted on the outer surfaces of each balloon.

FIG. 27 is a partial view in cross-section of an alternate embodiment of a drug delivery apparatus according to the present invention incorporating a plurality of balloons spaced longitudinally along a catheter body.

FIG. 28 is a partial view in cross-section of an alternate embodiment of a drug delivery apparatus according to the present invention incorporating a compartmentalized balloon.

FIG. 29 is partial view in cross-section of an alternate embodiment of a drug delivery apparatus according to the present invention incorporating a compartmentalized balloon.

DETAILED DESCRIPTION

Figure 4:
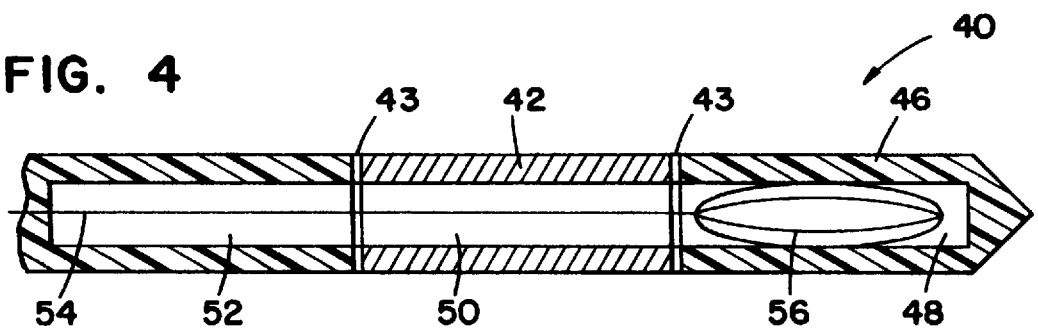
FIG. 4 is a partial cross-section of a further embodiment of the drug delivery apparatus of the present invention with a biased wire basket capable of expanding the polymer matrix.

A preferred embodiment as well as several alternative embodiments of the invention will be described in detail with reference to the drawings, wherein like reference numerals represent like parts and assemblies throughout the several views. Reference to these embodiments does not limit the scope of the invention, which is limited only by the scope of the claims.

FIGS. 1–31 illustrate the preferred and various alternate designs of the drug delivery apparatus in accordance with the present invention. In general, this apparatus provides a means and a system for delivering a drug or combination of drugs to or through a localized area of a passageway. The term drug includes any therapeutic agent such as a therapeutic drug, fixative, fixation solution, etc.

The apparatus also provides a means and a system to treat the localized area of the passageway or to treat a localized area of tissue located adjacent to the passageway, with minimal undesirable effect on other body tissue. The term "catheter" as used in the present application is intended to broadly include any medical device designed for percutaneous introduction and insertion into a body passageway or a localized area of internal tissue to permit injection or withdrawal of fluids, to keep passage open, to deliver drugs or other therapeutic agents, or for any other purpose. For purposes of this invention, a catheter is not necessarily tubular. It is contemplated that the drug delivery apparatus of the present invention has applicability for use with any body passageway or hollow organ including blood vessels, the urinary tract, the intestinal tract, the reproductive tract, the respiratory tract, etc.

Many of the embodiments are also capable of delivering a drug or combination of drugs to a localized area of internal body tissue. For this purpose the apparatus includes a catheter connected to a drug delivery component having a polymer matrix surrounding a transport means. The catheter may be flexible in order to enhance insertion into the passageway. The transport means is used to actively transport the drug from the polymer matrix to a target area of internal solid body tissue.

Catheters are commonly used in percutaneous transluminal coronary angioplasty (PTCA) procedures to dilate stenosed blood vessels or arteries. These include over-the-wire catheters of the type generally illustrated in U.S. Pat. No. 4,323,071, the disclosure of which is incorporated herein by reference; fixed-wire catheters of the type illustrated in U.S. Pat. No. 4,582,181, the disclosure of which is incorporated herein by reference; and rapid exchange catheters of the type illustrated in U.S. Pat. No. 4,762,129, the disclosure of which is incorporated by reference. These catheters may be modified according to the present invention.

To illustrate the method aspect of treating a localized area of a passageway, the specific application of the present invention to the reduction of restenosis is described below. Following a discussion of reducing restenosis, the treatment of tumors and erectile dysfunction is discussed.

As indicated above, PTCA is a highly successful procedure for the treatment of atherosclerosis, diseases, and other conditions that narrow arterial passageways. In normal PTCA procedure, a dilatation catheter is advanced along an artery to the desired position in the arterial system. The catheter includes an inflatable balloon at its distal end and means for inflating the balloon. When the balloon is positioned so that it traverses or crosses a stenotic lesion, the balloon is inflated to compress the atherosclerosis and expand the artery in a direction generally perpendicular to its wall. This action dilates the lumen of the artery. The balloon is then deflated and the catheter is withdrawn.

Despite the generally excellent success of PTCA, relatively high restenosis (the tendency of the dilated artery to close) rates are still a major problem. Abrupt reclosure of the artery as a result of thrombotic occlusion, vasospasms, or the like can also occur.

In accordance with the method of the present invention, a drug such as a fixation solution or a fixative is delivered locally to the dilated portion of the vessel to render the vessel wall biologically inert to prevent or reduce reactions that lead to reclosure. Examples of fixatives include, but are not limited to formaldehyde and glutaraldehyde. Because of the nature of the fixative and its ability to inactivate living cells and render the tissue in which it comes into contact biologically inert, it is essential that such fixative is exposed to only that portion of the arterial wall that was dilated. It is contemplated that drugs other than fixatives might be used to prevent restenosis or abrupt reclosure.

A preferred method and apparatus for delivering the drug locally to the dilated vessel is via a catheter modified according to the present invention. The catheter that delivers the drug may be the same catheter that dilates the vessel, thus combining both functions in one catheter. Alternatively, a vessel may be dilated first with a catheter designed specifically for dilation, followed by insertion of a second catheter for drug delivery. Modified catheters useful for either approach are illustrated in FIGS. 1–3, 8 or 9, all of which are described in detail below.

FIG. 1 illustrates the distal end of a catheter. The catheter includes an elongated, flexible catheter body 11, a drug delivery means in the form of a drug-impregnated polymer matrix 12 positioned in the catheter body 11 near its distal end.

In the embodiment illustrated in FIG. 1, impermeable end caps 17 are located on either end of the substantially cylindrical polymer matrix 12 to prevent movement of the drug in the matrix 12 longitudinally along the catheter body 11. The end caps 17 are, however, optional and may be added or removed as desired depending on the extent of leakage in the axial direction during drug transport and any undesirable effects that the leakage may have on the patient.

An electrode passageway 14 extends along the catheter body 11 on either side of the polymer matrix 12. A wire 16 is attached to the electrode 18 that is positioned in the distal end of passageway 14. The wire 16 extends from the proximal end of the catheter body 11 to its distal end where it is attached to electrode 18.

As used in the embodiments described with respect to FIGS. 1–10 in the present invention (all of which are designed to expand radially), the polymer matrix material used as the drug reservoir should be a compliant and expandable material that is, ideally, also non-compressible or minimally compressible. The material must be compliant and expandable to allow sufficient expansion of the polymer matrix material by the expansion means, whether the expansion means is an electrode 18 as in FIG. 1, wire basket 56 as in FIG. 5, wire basket 70 as in FIG. 7A or balloon 84 in FIG. 8.

The compressibility of the material is preferably limited to maximize the diameter of the catheter when the polymer matrix material is expanded, thus ensuring intimate contact between the polymer matrix and target tissue to enhance drug transfer. However, it is also contemplated that the polymer matrix material could be compressible, provided that the expansion means is designed to ensure intimate contact in spite of the compressibility of the polymer matrix material.

Figure 11:
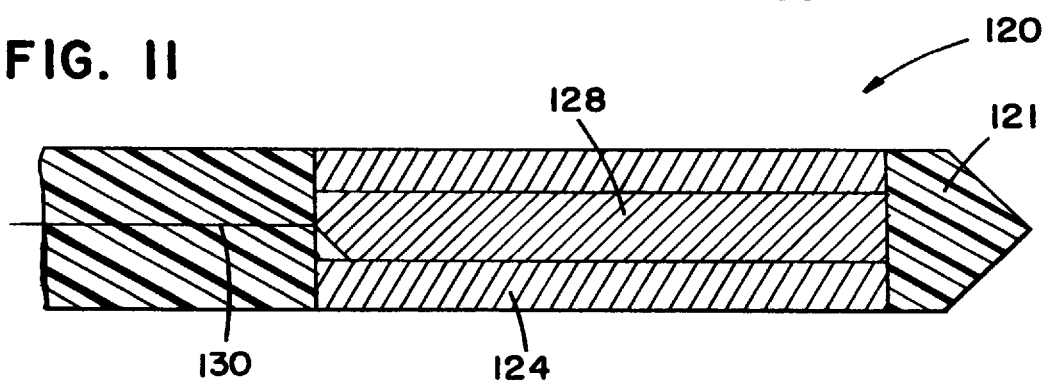
FIG. 11 is a partial cross-sectional view of a further embodiment of the drug delivery apparatus of the present invention designed for use in internal tissue where expansion of the polymer matrix is not needed to provide intimate contact.

In the embodiments that do not expand radially, one of which is illustrated in FIG. 11, it will be understood that the polymer matrix material need not be expandable or non-compressible and may, in fact, be rigid if desired.

As used in conjunction with the present invention, the term "polymer matrix" includes synthetic polymers in the form of hydrogels or other porous or drug-permeable configurations or morphologies, such as polyvinyl alcohol, polyvinylpyrrolidone and polyacrylamide, polyethylene oxide, poly(2-hydroxy ethyl methacrylate); natural polymers such as gums and starches; synthetic elastomers such as silicone rubber, polyurethane rubber; and natural rubbers. The above examples are provided for reference only, and the range of suitable polymer matrix materials should not be construed as limited to those materials listed above.

The polymer matrix material can also be hydrophilic or hydrophobic, provided it meets the physical characteristics described above.

Drugs may be incorporated into the polymer matrix material by a variety of methods. The drug can be incorporated into the material as the polymer solution or dispersion is formed into the preferred annular shape; it can be added to the polymer matrix material after formation into the desired shape either passively or actively (through, for example, such methods as iontophoresis); the drug can be dissolved in a solvent (e.g., water, propylene, glycol, etc.) and the resulting solution can be incorporated into the polymer matrix material; or the drug molecules can be incorporated directly into the polymer matrix material.

FIG. 2 illustrates the drug delivery apparatus of FIG. 1 with the polymer matrix 12 in its expanded state within an arterial vessel with walls 15. DuringpPTCA procedures, the catheter including the catheter body 11 and polymer matrix 12 is advanced to the desired position in the arterial system in which the polymer matrix 12 traverses or crosses the stenotic lesion. The matrix 12 is then expanded by pulling the electrode 18 into the interior chamber 13 of the polymer matrix 12. Wire 16 is preferably attached to a handle (not shown) at the proximal end of the catheter to allow electrode 18 to be pulled into the matrix 12. As a result, wire 16 is used to move electrode 18 into position in the matrix 12 (thereby expanding the matrix) as well as providing current to electrode 18 after the electrode is in place.

After expansion, the outer surfaces of the polymer matrix 12 press outwardly against the inner surfaces of the vessel wall 15 to expand or dilate the vessel in the area of the stenotic lesion. The drug in the matrix 12 is then transported into the surrounding tissue using iontophoresis.

Alternatively, catheters according to the present invention may be used to perform dilation of the vessel as well as deliver the drug to the targeted tissue.

In general, the preferred drug transport means is iontophoresis, which uses an electric potential or current to drive ionic drugs or drag nonionic drugs in an ionic solution. Iontophoresis is useful in the present invention because it facilitates both transport of the drug out of the polymer matrix 12 and tissue penetration.

In iontophoresis, two electrodes are used to develop the required potential or current flow. In particular, one electrode 18 (the "catheter electrode") is located inside of the polymer matrix 12 while the other electrode is located at a remote site on a patient's skin. The other electrode may also, in certain applications, be positioned at other regions of the patient. Iontophoresis is discussed in more detail below in relation to the embodiment shown in FIGS. 18–31.

In addition to constant direct current, other waveforms may be used (e.g., a series of rectangular waves producing a frequency of 100 Hz or greater) to accomplish the iontophoretic delivery process. A more complete description of iontophoresis and the alternate direct current waveforms useful in conjunction with the present invention can be found in U.S. patent application Ser. No. 07/957,209, filed on Oct. 6, 1992, titled INTERNAL IONTOPHORESIS ELECTRICAL CIRCUIT AND WAVEFORMS, by James E. Shapland and Keith Hildebrand, which is hereby incorporated by reference.

For iontophoresis techniques to be used, the drug within the polymer matrix 12 should have specific characteristics. Ideally, the drug should have an ionic nature or have other ionic molecules bound to the active components of the drug to promote the iontophoretic movement or transport from the polymer matrix 12. An electrical current for the iontophoretic process of FIG. 2 is produced between the electrodes 18 and 20 by an external power source 30 through the electrical leads 22 and 24, respectively.

In addition to drug delivery to internal tissue, the polarity of the iontophoretic electrodes may be reversed after treatment to recapture excess drug delivered to or through the vessel wall.

After transport of the drug from the polymer matrix 12 is completed, the electrode 18 is removed from the polymer matrix 12 and is preferably pulled into holding chamber 19 using wire 16 as shown in FIG. 3. Removing electrode 18 from polymer matrix 12 allows the matrix to assume its narrower profile, which aids in removal of the catheter from the vessel.

Those skilled in the art will realize that electrode 18 could also be stored in its original holding chamber 14 if a means of pushing electrode 18 into that chamber after use is provided. In the preferred embodiment however, the wire 16 used to supply power to the electrode 18 cannot supply a compressive force sufficient to push electrode 18 out of the polymer matrix 12. As a result, holding chamber 19 is used to store the electrode after wire 16 is used to pull electrode 18 into holding chamber 19.

Figure 5:
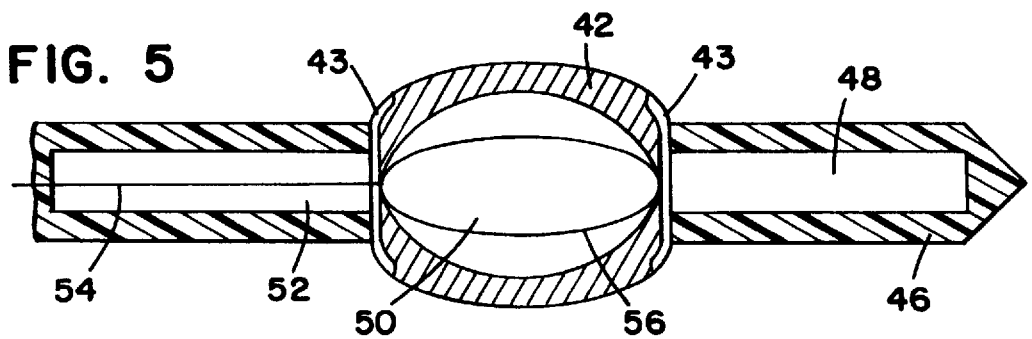
FIG. 5 is a partial cross-section of the embodiment of FIG. 4 with the polymer matrix expanded.
Figure 6:
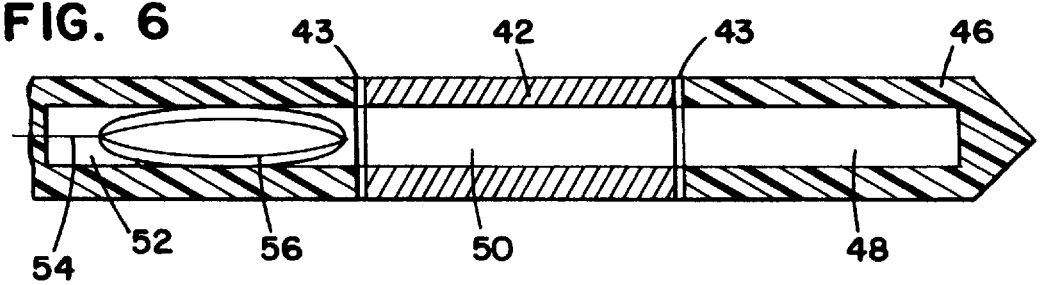
FIG. 6 is a partial cross-section of the embodiment of FIGS. 4 and 5, with the catheter prepared for removal.

FIGS. 4–6 depict an alternative embodiment of a catheter constructed according to the present invention. The primary difference between this catheter and the catheter of FIGS. 1–3 is the use of a spring loaded wire basket 56 that, prior to use, is stored in a holding chamber 48 constructed in catheter body 46. Construction of the polymer matrix 42 is substantially similar to that described with respect to the embodiment of FIGS. 1–3.

The polymer matrix 42 is provided in catheter body 46 in a substantially cylindrical shape. As with the preferred embodiments described above, optional impermeable end caps 43 are provided at either end of the polymer matrix to prevent transport of the drug contained in the polymer matrix 42 axially along the catheter body 46. The polymer matrix 42 is also provided with an interior cavity 50 for receiving the spring loaded basket 56. Opposite holding chamber 48 in catheter body 46 is holding chamber 52, which is used to store the spring loaded basket 56 after expansion of the polymer matrix 42. Storage of the compressed wire basket 56 in holding chamber 52 is depicted in FIG. 6.

In the preferred embodiment, spring loaded basket 56 also serves as an electrode for iontophoretic drug transport in addition to being used to expand the polymer matrix 42. Wire 54 provides electric current to the basket 56 during the iontophoresis process as well as moving the basket 56 between holding chamber 48, cavity 50 in polymer matrix 42 and holding chamber 52.

Referring to FIGS. 4–6, in use spring loaded basket 56 is drawn into chamber 50 in the polymer matrix 42 where it expands the polymer matrix. After expansion, the transport process is begun wherein current is provided to the electrode/spring loaded basket 56 via wire 54 to transport the drug from the polymer matrix 42 to the appropriate area. After the transport process is completed, the spring loaded basket is drawn further through the catheter body 46 into holding chamber 52, which allows the polymer matrix 42 to return to its narrower profile by compressing the spring loaded basket 56. Recompressing the spring loaded basket 56 to its narrower profile aids removal of the catheter from the vessel.

As with the embodiment depicted in FIGS. 1–3, the basket 56 is pulled into position using a wire 54 which is also used to provide current to the basket 56 during iontophoresis. As such, wire 54 cannot apply sufficient force to basket 56 to return it to cavity 48 after use. It will, however, be understood that if an appropriate mechanism to do so is used, chamber 52 would be unnecessary.

Figure 7A:
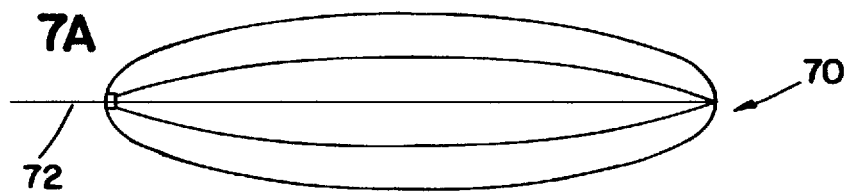
FIG. 7A is a schematic representation of a manually-loaded wire basket electrode for use in the present invention.
Figure 7B:
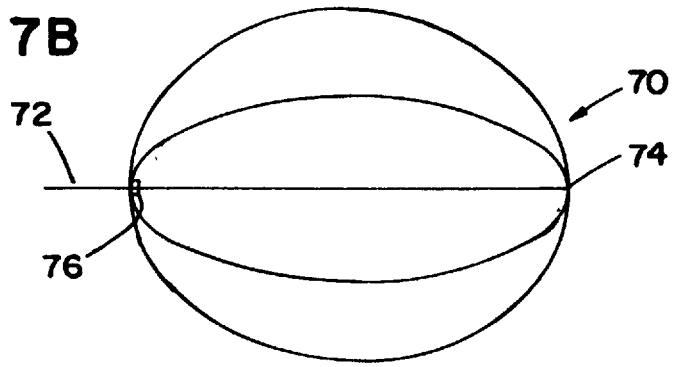
FIG. 7B is a schematic representation of the manually-loaded wire basket electrode of FIG. 7A in its expanded state.

FIGS. 7A and 7B depict an alternate embodiment of the wire basket design for use in the embodiments depicted in FIGS. 4–6. The basket 70 differs from the basket 56 of the embodiment depicted in FIGS. 4–6 in that it is manually-loaded as opposed to being spring-loaded. If a manually loaded basket 70 is used, it will be understood that holding chambers 48 and 52 depicted in FIGS. 4–6 would not be required as the basket would be manually expanded or relaxed as desired by the user.

FIG. 7A depicts the manually-loaded basket 70 in its relaxed or unexpanded state while FIG. 7B depicts the basket 70 in its expanded position. The basket is expanded by the use of force along wire 72 which extends through the basket to its distal end 74. The connection of the basket at point 76 along wire 72 is essentially a slip fit which allows point 76 to move along wire 72 when a force is applied to wire 72. As a result, the distance between points 74 and 76 is shortened, which translates into expansion of the diameter of the basket 70.

As with the spring-loaded basket, the manually loaded basket 70 also serves as the electrode when iontophoresis is used to supply the transport mechanism to transport drugs from the polymer matrix to the appropriate area.

One advantage of the manually-loaded basket 70 is the ability of the user to control the amount of expansion of the basket 70 by pulling a specific length of wire 72 from the catheter. In the preferred embodiment, the wire 72 is supplied with appropriate markings along its length to indicate expansion of the basket 70.

Figure 8A:
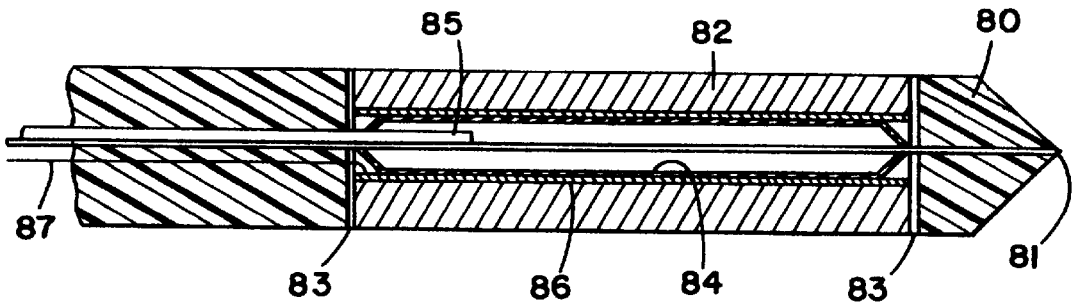
FIG. 8A is a partial cross-sectional view of a further embodiment of the drug delivery apparatus of the present invention incorporating a balloon to expand the polymer matrix and an expandable electrode placed between the balloon and the polymer matrix.
Figure 8B:
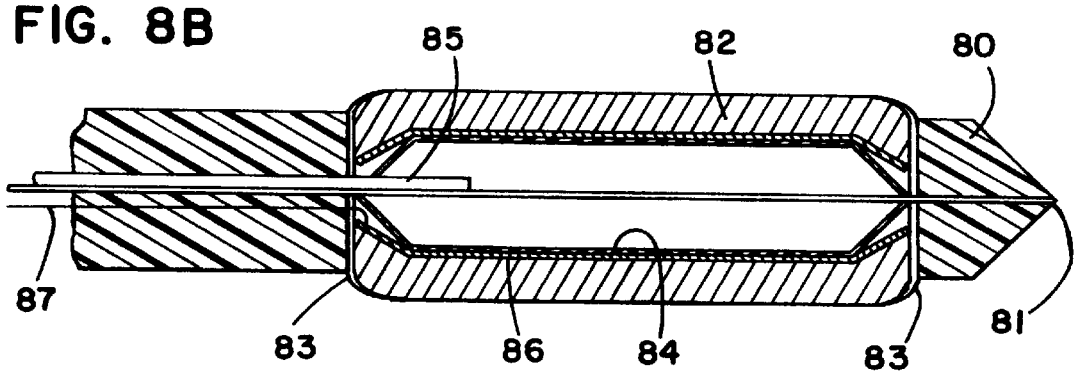
FIG. 8B is a partial cross-sectional view of the catheter of FIG. 8A in its expanded state.

The polymer matrix of the present invention can also be used in conjunction with a balloon to supply force to enlarge a vessel wall and/or provide intimate contact between a drug-impregnated polymer matrix and the vessel wall. Referring to FIGS. 8A and 8B, the embodiment depicted there includes a polymer matrix 82 located along a section of catheter body 80. Optional impermeable end caps 83 are located on either end of the substantially cylindrical polymer matrix 82 in the preferred embodiments. The center of the polymer matrix 82 contains an inflatable balloon 84 that is surrounded by a substantially cylindrical and expandable electrode 86, that could take the form of an expandable wire mesh.

In use, the balloon 84 is inflated through lumen 85 using any appropriate fluid or gas. In its expanded state, as depicted in FIG. 8B, electrode 86 expands with balloon 84 and is used to provide current to transport the drugs contained in the polymer matrix 82 to the surrounding tissue. Electric current is provided to the electrode 86 using wire 87 that runs alongside lumen 85.

Figure 9A:
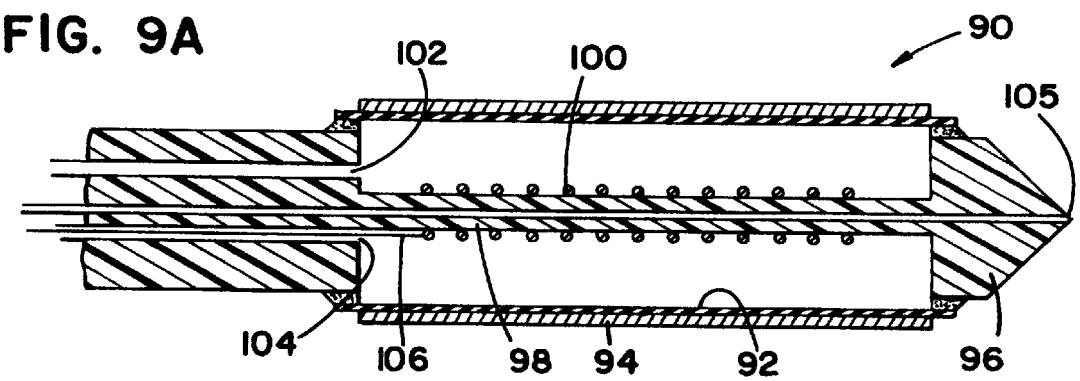
FIG. 9A is a partial cross-sectional view of a further embodiment of the drug delivery apparatus of the present invention incorporating a balloon for expansion and a central electrode.
Figure 9B:
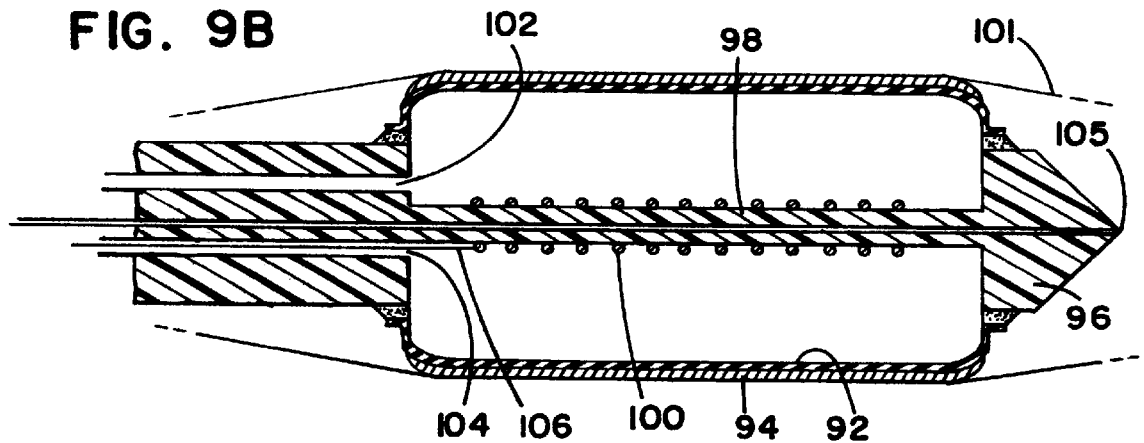
FIG. 9B is a partial cross-sectional view of the catheter of FIG. 9A in its expanded state.

FIGS. 9A and 9B depict an alternate embodiment of a catheter 90 incorporating a balloon 92 and polymer matrix material 94. In this embodiment, the catheter body 96 includes a core 98 extending through the balloon 92, around which the electrode 100 is wrapped in a coil fashion. Catheter body 96 also includes central guide wire lumen 105.

The balloon 92 consists of a substantially cylindrical section of a porous material that is attached along either end to the catheter body 96 using an adhesive or heat weld. The polymer matrix material 94 is disposed on the outer surface of the balloon 92 for intimate contact with a vessel wall 101 after expansion (see FIG. 9B).

In use, the balloon 92 is expanded with a fluid supplied through fluid-supply lumen 102 while wire lumen 104 houses the wire 106 that supplies current to the electrode. The fluid used to expand the balloon 92 is preferably either water or a weak electrolyte solution to enhance current flow through the polymer matrix material 94 that, in turn, enhances drug delivery to the target tissue.

Figure 10:
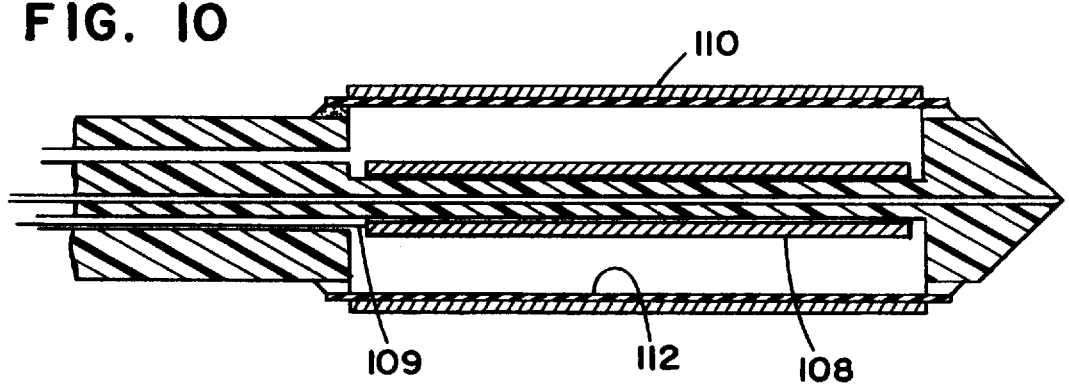
FIG. 10 is a partial cross-sectional view of a further embodiment of the drug delivery apparatus of the present invention incorporating a balloon for expansion and a transducer for phonophoresis.

FIG. 10 depicts a catheter substantially similar to the catheter 90 disclosed in FIGS. 9A and 9B, with the substitution of a transducer 108 for the electrode of catheter 90. The transducer 108 is used to produce sonic energy that moves drug from the polymer matrix material 110 using phonophoresis in the place of iontophoresis. Power is supplied to the transducer 108 using wire 109 that runs through a wire supply lumen.

The preferred fluids used for expansion of the balloon 112 include water or saline, although any fluid used to expand the balloon 112 need only provide the physical properties that enhance the propagation of sonic energy from the transducer 108 to the polymer matrix 110 and, finally, to the target tissue for delivery of the drug.

In addition to performing PCTA and preventing the reclosure of arteries, the catheter of the present invention can be used to deliver a variety of drugs in order to treat tumors, diseased tissue, damaged tissue, as well as other maladies. Examples of other drugs include, but are not limited to, antitumor agents such as the vinca alkaloids, anthracycline antibiotics, platinum analogs, antimetabolites (e.g., methotrexate); antibiotics; sensitizers or other compounds.

The preferred drug delivery apparatus 120 for treating internal body tissue includes a flexible catheter body 121 and substantially cylindrical polymer matrix 124. Positioned in the polymer matrix 124 is an electrode 128 that is connected to wire 130, which extends to the proximal end of the catheter 120.

In use, the catheter body 121 is moved into position. The drug is then driven out of the polymer matrix 124 by a voltage gradient (iontophoresis) using electrode 128.

It is to be understood that apparatus 120 can range in size from very large (trocar) to very small (tenths of mm), depending on the type and location of internal body tissue to be treated.

The embodiment in FIG. 11 preferably utilizes iontophoresis to drive the drug from the polymer matrix 124. Iontophoresis is preferred because it facilitates both transport of a drug and enhances tissue penetration. If iontophoresis is used, then similarly to the structure shown in FIG. 2, the catheter electrode 128 is located within the polymer matrix 124, while the other electrode (not shown) is preferably located on the body of the patient.

In addition to the performance of PTCA and the delivery of antitumor agents to internal tissues, one skilled in the art will appreciate the usefulness of the present apparatus and method for the treatment of other maladies associated with internal tissue. An example of such a malady is male erectile dysfunction.

FIG. 14 shows an alternative embodiment of the present invention that relates to a device for the treatment of male erectile dysfunction such as impotence. The device 210 is generally a catheter or probe 211 having a distal portion 212 and a proximal portion 213. The distal portion 212 has tip 215, and the proximal portion 213 has opposite tip 217. In a preferred embodiment, the length of the probe 211 is between 1 cm and 4 cm. The most preferred length is between 2 cm and 3 cm. However, one skilled in the art will realize that the preferred length can vary depending on the length of the urethra 214. An electrode 216 is operably connected to the probe 211 and covers most of the probers surface. Alternatively, the probe 211 could be coated with an electrically conductive material. The probe 211 should be made from an electrically insulated material. The electrode 216 or metalic coating is preferably made from platinum, gold, silver, or a combination of silver and silver chloride. A lead 218 is operably connected to the electrode 216, passes through the probe 211, and is then connected to a control box 220. The control box 220 contains a power supply and electronics for generating waveforms, i.e., a signal generator, which are not shown.

In an alternative embodiment, the probe 211 is formed from an electrically conductive material thereby eliminating the need for a separate electrode 216 or metalic coating. In this alterative embodiment, the lead 218 will pass an electric current directly to the probe.

A patch-type electrode 222 for placement on the skin of the patient is also attached to the control box 220 via lead 226. However, the patch-type electrode is preferably placed on the skin of the penis 224 or the thigh of the patient. The patch-type electrode 222 can be either reusable or disposable. However, a reusable electrode is preferred.

One skilled in the art will realize that the patch-type electrode 222 can be attached to the housing that contains the power supply and/or electronics for generating wave forms and thus form a single unit. The user would then hold the power supply housing against his body so that the electrode 222 would press against the skin of his thigh or penis. One skilled in the art will further realize that a circumferential penile band, not shown, is an alternative to the patch-type electrode 222.

A sheath 228 covers the probe 211 and the entire electrode 216. The sheath 228 is preferably made from a polymer matrix such as a hydrogel, which is lubricous and will aid the insertion and removal of the probe 211 into and out of the urethra 214. The sheath 228 might also include a porous inner membrane that can provide additional structure to support the hydrogel. Polymer matrices are discussed in more detail above. Preferably, the entire probe 211 and sheath combination is detachable from the lead 218 and disposable after use. In this embodiment, the lead 218 is preferable attached to the probe with a male/female connector, not shown. However, other types of connectors can be used. Alternatively, the sheath 228 is removable. Thus, the sheath 228 is disposable and the probe 211 is reusable.

The outer diameter of the sheath 228 is preferably between 2 mm and 3 mm when placed on the probe 211. The polymer matrix contains a drug that is effective for treating erectile dysfunction. An example is prostaglandins for the treatment of impotence. As described above, the drug must be either ionic or it must be mixed into an ionic solution. Additionally, the drug can be combined with other compounds such as cyclodextrins to increase solubility and enhance delivery. DMSO or protamine sulfate may also be used with the drug in order to enhance penetration across the urethra.

Removable sheaths or probe/sheath combinations that already contain the proper dose of drug might be sold at pharmacies. Alternatively, the user might soak the removable sheath in a solvent that contains the prescribed drug. The polymer matrix will then absorb the drug. The removable sheath 228 is then ready to use.

Alternative embodiments might include structures that will help control the flow of the drug from the polymer matrix and into the tissue. For example, the removable sheath 228 might contain nonporous end caps, which are discussed above. Additionally, only a portion of the removable sheath's 228 circumference might be electrically conductive. This configuration will help control the flow of drug from the polymer matrix toward the corpora cavernosa 232. The drug could then only escape through the electrically conductive portion of the removable sheath 228.

The probe 211 could include either a macroporous balloon or a microporous balloon as an alternative to the removable sheath. In this type of embodiment, the balloon preferably has pores over only a portion of its circumference. This configuration of pores will help control the flow of the drug toward the corpora cavernosa. Microporous and macroporous balloons were discussed in U.S. patent application Ser. No. 07/937,209.

As shown in FIG. 15, an alternative embodiment might include a disk or collar 234 that is substantially perpendicular to and circumscribes the proximal end of the probe 211. The collar 234 prevents the probe 211 from being inserted too far into the urethra 214. Collar 234 is located at a distance from the tip 215 that allows an appropriate length of the probe 211 to be inserted into the urethra. As discussed above, the collar 234 is most preferably between 1 cm and 4 cm from the tip 215, and most preferably between 2 cm and 3 cm from the tip 215. However, one skilled in the art will realize that the distance can vary according to the length of the urethra. Additionally, enough of the probe is between the collar 234 and the opposite tip 217 of the probe so that a user can grip the probe 211 in order to insert it and remove it from the urethra.

One skilled in the art will understand that there are other embodiments that can prevent the catheter from being inserted too far. For example, the diameter of the proximal portion 213 of the catheter might widen to a larger diameter than the distal portion 212. Alternatively, the proximal portion 213 might contain a stop leg that extends perpendicularly from the probe 211.

As further shown in FIG. 15, the proximal portion 213 of the probe 211 also has a handle 235 that is between collar 234 and opposite tip 217. The handle 235 allows the user to easily grip the probe 211 in order to insert the probe 211 into and withdraw the probe 211 from his urethra 214.

FIG. 16 shows another alternative embodiment. This embodiment includes a bi-polar electrode configuration that includes a first electrode 238, which is connected to a first lead 240 that extends through the catheter body 242 to the control box 220. The probe also includes a second electrode 244 and a third electrode 246 that are on oppositely disposed ends of the first electrode 238. The second electrode 244 and the third electrode 246 are both connected to a second lead 248, which in turn is connected to the control box 220. During drug delivery, the first electrode 238 has an opposite polarity from the second and third electrodes 244 and 246. One skilled in the art will realize that there are other electrode configurations. Bi-polar electrodes are discussed in more detail below.

Figure 18:
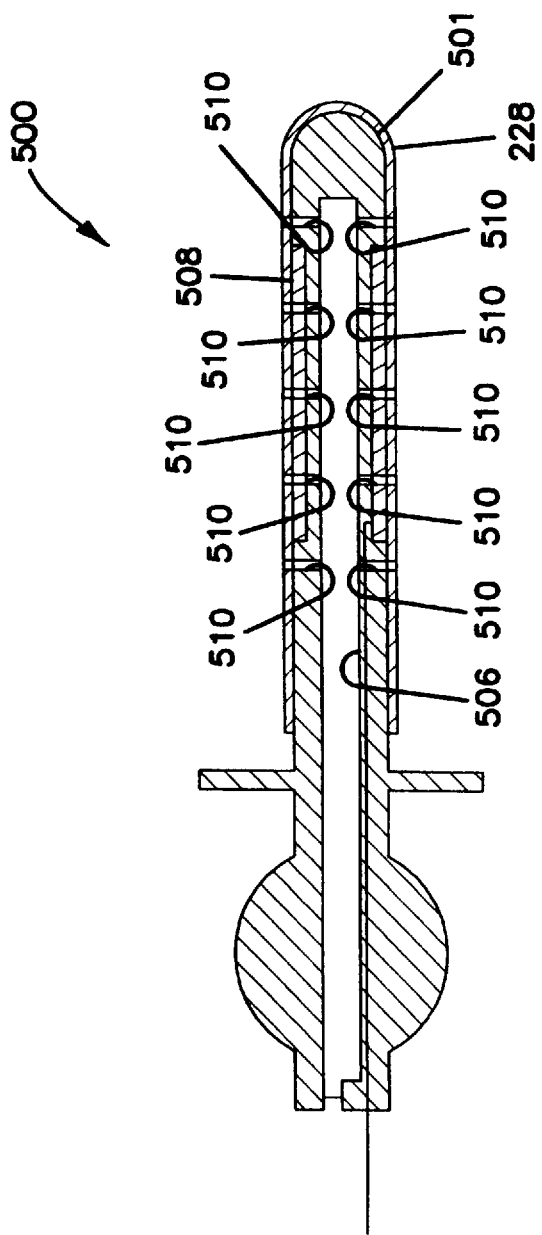
FIG. 18 is a partial view in cross-section of one embodiment of a drug delivery apparatus according to the present invention.

Another alternative embodiment is shown in FIG. 18. In this embodiment, a probe 500 has a cavity 506. Small apertures 510 pass from the cavity to the surface of the probe 501. The polymer matrix sheath 228 has an inside surface 508 that covers the apertures 510 in the surface of the probe 500. The probe 500 also has a larger hole 502 that passes from the cavity 506 to the surface 501 of the probe 500. A septum 504 seals the larger hole. In order to load the polymer matrix sheath 288 with a drug, the drug is injected through the septum 504 with a syringe. The drug will then pass into the cavity 506, through the small apertures 510, and into the polymer matrix sheath 228.

Proper use of the erectile dysfunction probe is shown in FIGS. 14 and 17. More specifically, the catheter is inserted 3 cm to 4 cm into the urethra 214. If only a portion of the removable sheath 228 is electrically conductive, then that portion should be facing toward the top of the penis 224 so that the drug has a direct path to the corpora cavernosa 232. The patch-type electrode 222 is then placed on the top of the penis 224 so that it is directly over the probe 211. There should not be any hair between the patch-type electrode 222 and the skin. If a bi-polar design is used (FIG. 16), the application of the patch-type electrode 222 is not necessary.

After the probe 211 and patch-type electrode 222 are in place, the control box 220 is activated so that an electrical current will flow between the electrodes 216 and 222 and through the corpora cavernosa 232. The electrical current will transport the drug from the removable sheath 228, through the tissue of the penis 224, and into the corpora cavernosa 232. An erection should occur almost immediately, and thus the control box 220 should be activated for only a few seconds to a few minutes. After the treatment is complete, the probe 211 and the patch-type electrode 222 should be removed.

The electrical current is preferably between 0.1 mA and 20 mA and can have either direct current or a waveform with a frequency preferably between 0 and 500 KHz. The preferred duty cycle of a waveform is between 20% and 80%.

A variety of waveforms can be used with the present invention including square waves and sawtooth waves. Wave forms are discussed in more detail in U.S. patent application Ser. No. 08/110,109, filed Aug. 20, 1993 and entitled SYNCHRONOUS IONTOPHORESIS DRUG DELIVERY, which is hereby incorporated be reference.

When the probe 211 is inserted into the urethra 230, the removable sheath 228 should be in intimate contact with the urethral mucosa 250. In order to ensure contact, an alternative embodiment might include expansion means such as an inflatable balloon, an expandable basket, or a slidable electrode. These expansion means are describe in more detail above.

In the case of the vascular delivery embodiments (FIGS. 1–9), the tissue delivery embodiment (FIG. 11), and the erectile dysfunction embodiment (FIGS. 14–17), described above, phonophoresis (sometimes referred to as sonophoresis) can be used as an alternative to iontophoresis to transport drugs from the polymer matrix into the surrounding tissue.

Phonophoresis is the use of ultrasonic or high frequency sound waves to transport therapeutic agents that include non-ionized molecules. Prior applications of phonophoresis have been limited to transdermal delivery of drugs such as anti-inflammatory agents and local anesthetics through the skin to treat epicondylitis, tendonitis, bursitis and osteoarthritis.

Phonophoresis is also well-suited for driving therapeutic agents from the polymer matrix material of the present invention to localized body passageways or internal tissues because it facilitates both transport of a drug from the polymer matrix and enhances tissue penetration. In addition to drug delivery, ultrasound may be advantageously used with the catheter of the present invention based on the increased tissue temperature, tissue hyperemia and increased capillary permeability associated with ultrasound. These actions can enhance intra-tissue drug transport and cellular uptake as well as cause vasodilation/relaxation which may be beneficial in vascular drug applications using catheter embodiments of the type described herein.

When phonophoresis is used with either the vascular delivery embodiment or tissue delivery embodiment of the catheter of the present invention, the electrode is replaced by an ultrasonic piezoelectric transducer (barium titanate, lead zirconate titanate, or the like), which is connected to the external power source. After the catheter is in place, the ultrasonic transducer is activated to transport drugs into tissue surrounding the catheter.

The diffusion rate of drugs delivered by phonophoresis depends upon the intensity and frequency of the ultrasonic field. Prior transdermal applications of phonophoresis use intensities of 0.1 to 6 watts/cm$^2$ and involve direct correlation between the amount of drug diffused and the intensity of the ultrasonic field. Internal applications (not requiring transdermal delivery) of phonophoresis with the catheter embodiments of the present invention are envisioned to require significantly less intensity to deliver an equal amount of drug. Various frequencies can be used. It is envisioned that approximately 20 MHz or less can be used for internal applications of the catheter embodiments described herein. However, a frequency of 1 MHz to 10 MHz is probably most appropriate depending on the therapeutic agent and the type of treatment for which the catheter is used.

In addition to the substitution of phonophoresis for iontophoresis as described above, an additional feature that can be incorporated in catheters according to the present invention is a protective covering over the polymer matrix material. A protective covering may be useful with some polymer matrix materials which are not as dimensionally stable as others and could be particularly sensitive to shearing and/or abrasion during insertion and removal. The shearing and/or abrasion may cause portions of the polymer matrix material to remain in the patient after treatment.

Figure 12A:
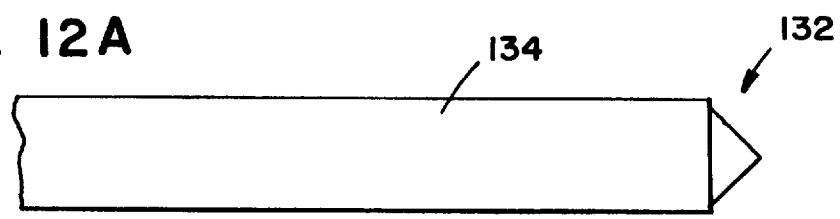
FIG. 12A is a view of a further embodiment of the drug delivery apparatus of the present invention incorporating a movable sheath for protection of the polymer matrix.
Figure 12B:
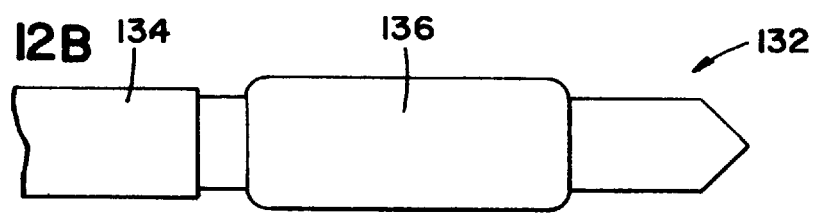
FIG. 12B is a view of the catheter of FIG. 12A with the sheath retracted and the polymer matrix exposed for drug delivery.

To prevent that occurrence, catheters according to the present invention can be fitted with protective coverings that take a number of forms. One version of a protective covering is depicted in FIGS. 12A and 12B, where the catheter 132 includes an outer sheath 134 that covers the polymer matrix 136 during insertion of the catheter 132. After the catheter 132 is in position, the sheath 134 is retracted to expose the polymer matrix 136 and drug delivery can proceed (either with expansion of the polymer matrix as depicted in FIG. 12B or with delivery of the drug without expansion). After treatment, the sheath 134 is then extended to again protect the polymer matrix 136 during removal of the catheter 132.

The sheath 134 in this embodiment of the protective covering is preferably constructed of a rigid material to provide consistent retraction and extension characteristics. An additional advantage of the sheath 134 is that the material used for its construction is also typically impermeable to the drug contained in the polymer matrix 136. That impermeability prevents delivery of the drug in the polymer matrix through passive diffusion to tissue encountered during insertion or removal of the catheter 132, thus enhancing the dosage accuracy of the catheter 132.

Figure 13:
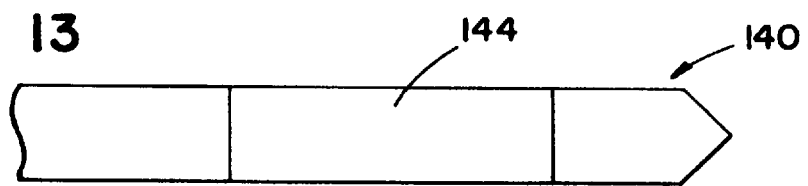
FIG. 13 is a view of a further embodiment of the drug delivery apparatus of the present invention incorporating a porous outer membrane for protection of the polymer matrix.

An alternate protective covering is depicted in FIG. 13, where an outer membrane 144 covers a polymer matrix (not shown) in catheter 140. It will be understood that catheter 140 could take the form of any of the catheters described in detail above. The membrane 144 is porous to the drug contained in the polymer matrix to allow transfer through the membrane 144 using either iontophoresis or phonophoresis.

If outer membrane 144 is constructed of a flexible material it can be used in catheters in which the polymer matrix material 142 is expanded with an electrode, transducer, wire basket or inner balloon (all of which are described in detail above). If expandable, the membrane 144 can be loosely fit around the polymer matrix to allow room for expansion. In the alternative, if the membrane 144 is elastic or stretchable, its fit around the polymer matrix can be tighter as the membrane can then stretch around the expanded polymer matrix.

As with the rigid retractable sheath, the porous membrane 144 also protects the polymer matrix from shearing and abrasion and also offers some degree of protection from passive diffusion during insertion and removal of the catheter 140 (although the membrane 144 is porous by its very nature).

It will also be understood that portions of the membrane 144 can be impermeable (non-porous) to further control delivery of the drug in the polymer matrix. In particular, the impermeable portions would preferably located on either end of the membrane 144 to limit or prevent drug delivery in an axial direction along the body of the catheter 140. This design is particularly useful in expanding catheters, as after expansion of the polymer matrix and associated membrane 144, the porous portions of the membrane 144 would be in intimate contact with the vessel wall or target tissue, while the remaining sections of membrane 144 which are not in intimate contact would be impermeable, thereby limiting unwanted drug transfer in the axial direction.

FIGS. 19–32 illustrate alternate embodiments of drug delivery apparatus. The apparatuses provide a means for percutaneously introducing and delivering a drug or combination of drugs to, or through, a localized area of a passageway, a localized area of tissue outside of a passageway or a localized area of tissue, with the delivery being enhanced using electric current/potential provided by a plurality of internal electrodes.

All apparatus according to the alternative embodiments rely, at least in part, on electric current/potential to enhance delivery of the drug into tissue surrounding the distal ends of the catheters. Tontophoresis is the more common method of using electric current/potential to enhance drug delivery, although the present invention also contemplates the use of any other method of providing electric current/potential (such as electroporation) within a patient to enhance localized internal drug delivery.

In addition to driving drugs from the polymer matrix, iontophoresis may be used in the alternative embodiments to carry ionic drugs through a permeable membrane. Thus, iontophoresis uses electric current/potential across a permeable membrane to drive ionic drugs through the membrane and into the desired tissue. Iontophoresis can facilitate transport of a drug across a permeable membrane as well as enhance tissue penetration.

Alternatively, however, the drug can consist of essentially neutral molecules, but may still be delivered by electric current/potential. It is theorized that the movement of the drug (in solution in the water) is aided by the movement of sodium ions in the water in an electric field. As used herein, the term "iontophoresis" is meant to broadly include iontophoresis and similar effects.

In the application of iontophoresis, two electrodes, one on each side of the barrier, are utilized to develop the required potential or current flow. In particular, one electrode, the supply electrode, is located inside of the catheter in opposed relation to the drug delivery wall of the catheter while the other electrode, the return electrode, is located at any site within the patient.

Both of the electrodes, and any additional electrodes used for iontophoresis, are located within the patient to avoid the disadvantages associated with providing electric current across the patient's skin. For the purposes of the present invention, internal electrodes include, but are not limited to: those placed within the patient's gastro-intestinal tract under the surface of the patient's skin (subcutaneous); etc.; even though such placements may not be medically considered "internal" to the patient.

FIGS. 19 and 20 illustrate one preferred embodiment of a catheter employing multiple internal electrodes. The catheter 310 comprises an elongated catheter body 312 and an inflatable balloon 314 forming a drug delivery means located proximate the distal end catheter body 312. A supply electrode 316 is located on catheter body 312 within balloon chamber 314.

At least one return electrode 320 is placed on the outer surface of balloon 314. Reference may be made to FIG. 19 which depicts a plurality of return electrodes 320 located about the circumference of balloon 314. The return electrodes 320 preferably run longitudinally along the outer surface of balloon 314. They can be comprised of many different materials, all of which are electrically conductive. As balloon 314 is typically flexible, each return electrode 320 also will be typically flexible and may consist of a wire, electrically conducting paint, ink, or a thin conductive coating that is sputtered or otherwise deposited on the surface of balloon 314.

Balloon 314 itself is permeable to allow transport of a drug from within the balloon 314 to body tissue surrounding the balloon. The drug is typically provided within balloon 314 through a lumen that is defined in catheter body 312 and that opens within balloon 314.

Because balloon material 314 is permeable, each of the return electrodes 320 preferably reside on an insulating layer 322 between the return electrodes 320 and balloon 314. The insulating layer 322 prevents current from running directly between supply electrode 316 and the return electrodes 320 placed on the outer surface of balloon 314. Furthermore, the insulating layer 322 can serve as an intermediate adhesion layer where the electrode materials will not adhere to the balloon 314.

The width of the insulating layers 322 underneath the return electrodes 320 can be varied to control the shape of the electric field external to the balloon. Typically, the wider the insulation layer, the greater the tendency for drugs to be transported radially away from the catheter body. That advantage is, however, countered by a shadow effect that is experienced directly external to the insulation layer. Drug transport into a shadow area is not as effective as in areas outside of the shadow. As a result, any design must balance the desirable characteristics of providing an increased insulation layer with the disadvantages associated with wider insulation.

One alternative to providing insulating layers 322 beneath return electrodes 320 is to provide balloon 314 with appropriate areas under return electrodes 320, that are impermeable.

Each of the return electrodes 320 is preferably in electrical communication along the body of catheter 312 for connection to a means of providing electric current/potential. As depicted in FIG. 18, the return electrodes 320 extend down to catheter body 312 at one end of balloon 314 to a common return electrode 318 that is then connected to the appropriate electrical current/potential source.

FIG. 21 depicts an alternate embodiment of a device similar to that depicted in FIGS. 19 and 20. The essential variation between catheter 330 in FIG. 21 and catheter 310 in FIG. 19 is the shape and placement of return electrodes 332. As depicted in FIG. 21, a plurality of substantially circumferential return electrode 332 are deposited on the outer surface of balloon wall 334. Each of the return electrodes 332 is electrically connected using one or more longitudinal electrodes 336 that are also deposited on the surface of balloon 334.

An alternate embodiment of an apparatus according to the present invention is depicted in FIG. 22. As shown there, the apparatus includes impermeable end sections in the balloon wall 344. Impermeable end sections in catheter balloons including centralized porous sections are described in U.S. Pat. No. 5,286,254, which is entitled DRUG DELIVERY APPARATUS AND METHOD. The present invention takes that structure and adds surface return electrodes 342 located on either end of the porous central section of balloon 344. The surface return electrodes 342 are used in conjunction with supply electrode 346 to enhance drug delivery using electric current/potential.

The methods of providing a pair of circumferential return electrodes 342 include the deposition of a thin circumferential layer of an appropriate conductive material on the surface of balloon 344 and connecting the same through the catheter body to an electric current potential source or coating the entire end sections of the balloons 344 with the conductive material and then providing an insulating layer over those portions of the conductive layer that are not to be exposed.

It will, of course, be understood that an insulating layer must be also provided underneath the conductive layers on the outer surface of balloon 344, unless the balloon 344 is impermeable at its ends, in which case, the balloon wall 344 will typically provide the necessary insulation between return electrodes 342 and supply electrode 346.

Although the device pictured in FIG. 22 includes a plurality of return electrodes 342, it will be understood that only one return electrode 342 may be provided, particularly in situations where the electric field provided between supply electrode 346 and return electrode 342 is sufficient with only a single electrode 342. Furthermore, although two return electrodes 342 are shown, it will be understood that more than two such electrodes could also be provided.

Yet another alternate embodiment of a catheter 340 can be described with reference to FIG. 22. This embodiment will be particularly useful for delivering drugs that exhibit a negative charge. Similar to the embodiment described above, the catheter 340 will include a permeable section between return electrodes 342 located on the outer surface of balloon 344.

In this embodiment, the end sections of balloon 344 will be also provided as permeable. As a result, end sections of balloon 344 will preferably exhibit a negative charge and the only positively charged surfaces will be those defined by return electrodes 342. As a result, the pro-coagulant surfaces of positively-charged electrodes 342 will be surrounded by negatively charged surfaces in porous sections of balloon 344.

Providing permeable end sections will result in drug delivery in a direction longitudinal along the catheter 340. In many cases, the drug delivery will be allowable or even desirable.

Where, however, delivery of the drug through porous end regions is not desired, methods of controlling the transport of drug through the end sections can be provided. They could include fabricating the end sections of balloon walls 344 with a limited pore density or pore size as compared to those pore sizes and densities provided in the central section of balloon 344 between electrodes 342. Pore size and density could be controlled to allow the end sections to provide adequate electrical conductivity in the end sections in balloon wall 344, while preventing or limiting bulk movement of the drug out of the end sections of balloon wall 344.

Other methods of inhibiting flow through the end portions of balloon 344 are also contemplated. Examples include, but are not limited to: applying coatings to the end sections of balloon 344 that sterically block bulk flow of drugs out of the end sections of balloon 344. The coating may also have a charge of the same polarity as the drug desired to be delivered, thereby inhibiting movement of the drug through the coating due to the repellant forces between the similarly-charged coating and drug molecules.

FIG. 23 depicts yet another alternate embodiment of a catheter 350 constructed according to the present invention. Essentially, catheter 350 is similar in construction to the catheters depicted in FIGS. 19–22 with the primary difference lying in the pattern in which return electrode 352 is provided. As shown return electrode 352 is provided in a helical pattern running along the outer surface of balloon 354. It will be understood that electrodes on the exterior of the balloon can be provided in any pattern according to the present invention and that the patterns depicted herein should not be construed as limiting the scope of the present invention.

One potential disadvantage to providing internal electrodes that are exposed to blood is the generation of thrombosis at the electrode surfaces. Thrombin activity is particularly troublesome with those electrodes that are positively charged. Drug delivery apparatuses constructed according to the present invention, however, can be provided that reduce or eliminate thrombosis caused by positively charged electrodes and/or surfaces.

FIG. 29 depicts the cross-section of a return electrode 360 placed on insulating layer 362 that is, in turn, located on a balloon 364. Electrode 360 is coated with a thrombo-resistant material 366 to produce or eliminate thrombin activity. Typically, the thrombo-resistant material is a polymer coating. Thrombo-resistant polymeric materials include, but are not limited to: polyethylene glycol, polyethylene oxide, numerous hydrogels, and several polyurethanes. In addition, drugs intended to inhibit thrombosis and restenosis can be incorporated into the thrombo-resistant polymeric biomaterials. Examples of such drugs are also known and include, but are not limited to: heparin, hirudin, PPACK, antisense oligonucleotides, as well as other inhibitors of thrombin activity, or cell proliferation. In some applications, these compounds actually may be delivered to the target tissue from the thrombo-resistant polymer 366 using the electric current/potential used to deliver the drugs within the catheter itself.

FIG. 25 is a longitudinal cross-sectional view of yet another alternative embodiment of a catheter according to the present invention that may be useful for reducing thrombosis. As depicted, catheter 370 includes catheter body 371 on which balloon 372 is located. Balloon 372 forms drug delivery means and can be made from a permeable or an impermeable membrane. If permeable, drugs can be delivered through balloon 372 as well as from polymer matrix materials 374 deposited on the outermost surface of balloon 372. The outer surface of balloon 372 is coated first with an electrically conductive coating 376 on which the polymer matrix material 374 incorporating a drug is applied. Coating 376 functions as the supply electrode for catheter 370.

A return electrode 378 is typically along catheter body 371 and is preferably coated with a layer 379 of a thrombo-resistant material such as those described in the description of FIG. 24 above.

The polymer matrix material 374 on balloon 372 could also include thrombo-resistant materials if necessary. Those skilled in the art will, of course, recognize that thrombo-resistant materials are most importantly placed on those electrodes that are positively charged during any drug delivery process.

Furthermore, the catheter 370 of FIG. 25 can be used to deliver two separate drugs simultaneously. In that embodiment, polymer matrix material 374 and the coating 379 on return electrode 378 can incorporate different drugs where each drug is delivered most efficiently using oppositely charged electrodes.

In addition, changes in electrode polarity can also be useful to retain the drugs within the material 374 or 379 until the catheter 370 is in the correct position for drug delivery to occur, at which time, the polarity of electrodes 378 and 374 can be reversed to begin drug delivery.

A further alternate embodiment of a catheter 380 is depicted in FIG. 26. As shown there, the catheter 380 includes a dual concentric balloon design for the drug delivery means comprising a non-permeable inner balloon 382 and a permeable outer balloon 386. At least a portion of the outer surface of inner balloon 382 includes a supply electrode 383 deposited thereon. Likewise, at least a portion of the outer surface of outer balloon 386 also includes a return electrode 387 deposited thereon. It will be understood that at least a portion of outer balloon 386 must be permeable and free of any conductive electrode 387. Alternatively, the return electrode could be positioned off the outer surface of permeable balloon 386.

Preferably, each of the electrodes 383 and 387 comprises a thin conductive coating placed on the respective balloons and is flexible with the same. Inner balloon 382 and outer balloon 386 define an intermediate volume 384 in which a drug can be placed in solution or can be maintained within material that can be loaded with a drug solution, such as a polymer matrix material. If the drug within the volume 384 is in solution, it can be delivered via a lumen or can be provided within the volume 384 and driven out through balloon 386 using pressure in balloon 382 as well as electric current/potential between supply and return electrodes. Furthermore, that pressure can also supply dilatation capabilities to catheter 380 when the pressure of outer balloon 386 is sufficient to dilate a vessel in which catheter 380 is located.

When activated, supply electrode 383 is used to drive the drug out through outer balloon 386 and into tissue surrounding catheter 380. The design of catheter 380 can be particularly helpful if thrombosis is considered a problem and the drug to be delivered is positively charged. In that situation, the positive supply electrode can be designated as electrode 383 on inner balloon 382, which effectively shields the most positively charged surfaces from contact with a patient's blood.

Further variations in the design of catheter 380 include a permeable inner balloon 382 that includes very small pores large enough to allow the passage of electric current, but small enough to restrict the flow of drugs through the balloon 382. In that variation, the inner electrode is located within the volume defined by inner balloon 382 that is also occupied by saline or another conducting fluid to promote the flow of current between the supply and return electrodes.

FIG. 27 depicts another alternate embodiment of a catheter according to the present invention. The drug delivery means of catheter 390 includes two balloons 392 and 394 spaced longitudinally along catheter body 391. Each balloon contains its own electrode 393 or 395. In use, the electrodes are oppositely charged and drugs within either one of the balloons can be driven out of the same and into tissue surrounding catheter 390.

Catheter 390 is particularly useful in those situations in which two drugs are desired to be delivered simultaneously using electric current/potential. In those situations, it will be understood that one of the drugs should be acidic (i.e., exhibit a partial negative charge at neutral pH). Each drug would be located in the appropriate balloon 392 or 394, and the electrodes 393 and 395 would be provided with the appropriate polarity when delivery commences, thereby driving the drugs out of their respective balloons.

This embodiment may be especially useful where regulatory restrictions may prohibit the mixing of two oppositely-charged drugs within a single drug solution cocktail for simultaneous delivery through a single porous balloon. Furthermore, this embodiment also eliminates the need for delivering one of the drugs through a single balloon catheter and then sequentially delivering a second drug through the same balloon catheter, thus saving time in the administration of more than one drug to internal body tissue.

In those situations where only one of the balloons 392 or 394 is provided with a drug solution for delivery, it will be understood that the remaining balloon 392 or 394 would be filled with a saline solution or other similar electrically conducting fluid. In that embodiment, the balloon containing the saline solution would exist primarily to prevent contact between the positive electrode and the patient's blood.

Furthermore, it will be understood that the saline filled balloon could be made extremely porous and saline infused through the balloon to provide positive pressure therein, further reducing the chance for contact between a positively charged electrode within the balloon and the patient's blood.

In yet another embodiment, either of balloons 392 and 394 could be impermeable and provided with an electrode on its outer surface. The impermeable balloon could then be used to dilate a vessel through pressure after or before which drug delivery could occur.

It will also be understood that any number of balloons could be spaced longitudinally along a catheter body 391 and that the device pictured in FIG. 26 should not be construed as limiting the present invention to catheters having only two such balloons spaced longitudinally.

FIG. 28 depicts yet another further embodiment of a catheter according to the present invention. The catheter 400 includes a single balloon 402 for drug delivery means located along a catheter body 401. The balloon 402 is divided into three compartments 403, 405 and 407. Compartments 403 and 405 each contain electrodes 404 which have the same polarity. Compartment 407 includes an oppositely charged electrode 406. The two outer compartments 403 and 405 are separated from inner compartment 407 by baffles 408 located within balloon 402.

In use, chamber 407 is preferably filled with saline solution or another conductive fluid and electrode 406 is positively charged while outer compartments 403 and 405 are filled with the same or different drugs and outer electrodes 404 are negatively charged. In that method, the risk of inducing thrombosis is reduced as the positively charged surface of balloon 402 is located furthest from contact with the patient's blood.

Furthermore, the length of balloon 402, measured longitudinally along body 401 is preferably minimized to provide near uniform distribution of the drug within the target tissue surrounding balloon 402.

FIG. 29 depicts an alternate embodiment of a catheter 410 according to the present invention which varies from catheter 400 depicted in FIG. 28 above only in the shape of baffles 418. As depicted, baffles 418 preferably comprise rounded chambers which may be inflated separately from outer balloon 412 using separate lumens (not shown). The chambers 418 may be attached to the inner surface of balloon 412 or they may be attached only along catheter body 411 in which case the pressure within baffles 418 is relied on to seal compartments 413 and 415 from central compartment 417.

Figure 30:
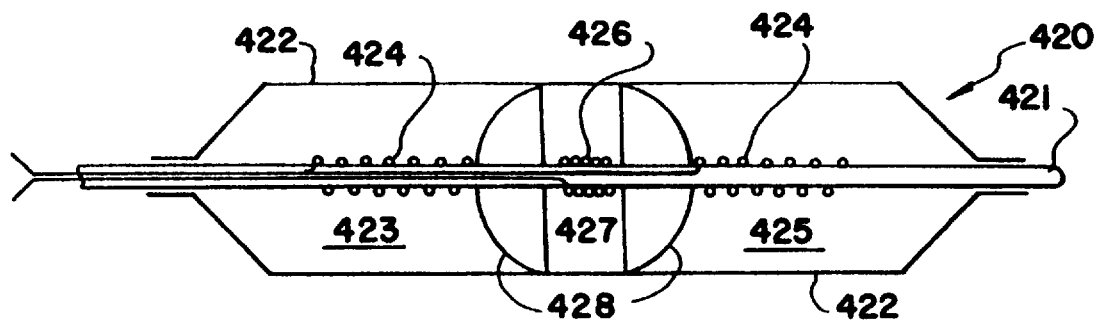
FIG. 30 is a partial view in cross-section of an alternate embodiment of a drug delivery apparatus according to the present invention incorporating a compartmentalized balloon.

FIG. 30 depicts yet another further alternate embodiment of catheter 420 constructed similar to the catheters depicted in FIGS. 29 and 29. The primary difference between catheter 420 depicted in FIG. 30 and catheter 410 depicted in FIG. 29 is the shape of the baffles 428. Baffles 428 in catheter 420 preferably comprise essentially hemispherical volumes to reduce the volume of central compartment 427. Reducing the volume of the central compartment 427 may enhance the uniformity of drug delivery from the outer compartments 423 and 425.

Like the design of catheter 390 depicted in FIG. 27, it will be understood that any of the catheters 400, 410 and 420 could be designed with more than three compartments in that the present invention should not be construed as limited to compartmentalized balloon catheters having only three compartments. Any number of compartments could be provided where necessary or desired.

Figure 31:
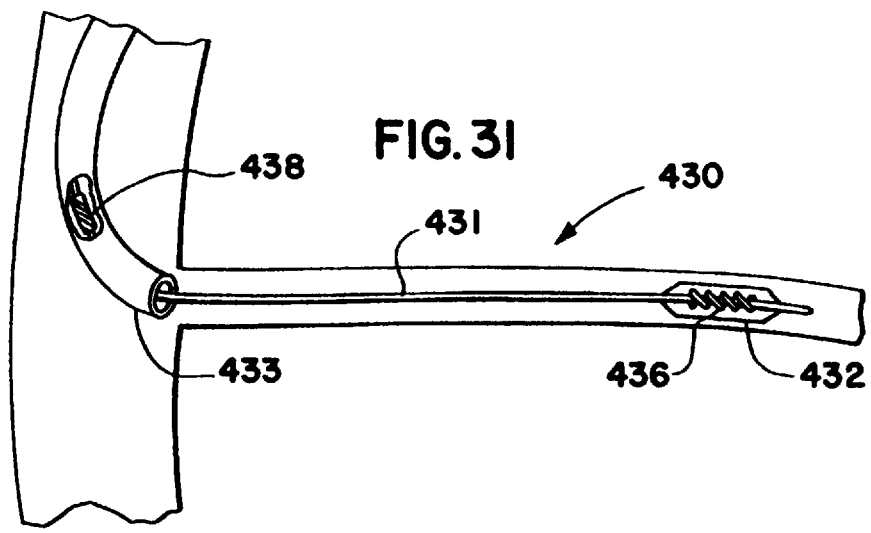
FIG. 31 is a schematic diagram of one embodiment of an apparatus according to the present invention.

FIG. 31 is a schematic diagram of yet another alternate embodiment of a catheter 430 according to the present invention which includes an elongated body 431 with the drug delivery means comprising a balloon 432 attached to the distal end. Balloon 432 contains an electrode 436 used in conjunction with electric current/voltage to enhance transport of drugs from balloon 332 into the tissue surrounding the same.

In this embodiment, the return electrode 438 is located within a guiding catheter 433. In the preferred method, guiding catheter 433 extends only up to the junction between the aorta and a coronary sinus. Return electrode 438 is located within the guiding catheter 433 to reduce its contact with a patient's blood. In that way, the induction of thrombosis within the patient's blood can be minimized.

It will be understood that the return electrode 438 could be provided in many forms. Examples include, but are not limited to: conductive coatings on the inner surface of the guide catheter 433 or the outer surface of the catheter body 431, any metal used in construction of guide catheter 433, treatment catheter 430 or any guidewire (not shown) that remains within guide catheter 433 could be exposed, etc.

Further, in a more preferred embodiment and method, saline or another solution is infused through guiding catheter 433 to provide positive pressure which further limits the ability of blood to travel up the guiding catheter 433 to contact the return electrode 438 located within guiding catheter 433.

In some situations, the tip of a guidewire (not shown) include an exposed metal portion that serves as the return electrode, with at least one supply electrode 436 being located within the drug delivery chamber of the catheter 430. In this embodiment, the guidewire preferably provides the negative charge to reduce the creation of thrombosis on the exposed guidewire electrode within the patient's blood.

All of the various embodiments of catheters in FIGS. 19–32 include a multiple number of internal electrodes designed to provide the apparatus necessary for iontophoresis and/or electroporation without the disadvantages associated with the use of an external electrode. In addition to the embodiments described above, it will be understood that the electrodes not located in or near the drug delivery area can be located anywhere within the patient's body, provided that they are not located on the exterior of the patient such that the high impedance associated with skin can be avoided.

Examples of such internally placed electrodes include, but are not limited to: subcutaneous needle electrodes, electrodes attached to other devices inserted into the patient such as pacing leads, defibrillator leads, IV lines, etc. One particular version of such an internally located electrode could be incorporated on the outer surface of the introducer sheath used for percutaneous delivery of catheters according to the present invention. One particular advantage of that electrode design, as well as any other electrode residing in tissue as opposed to within a blood vessel, is the limited exposure such electrodes would have to blood which should further reduce the potential for thrombosis.

Examples of additional iontophoresis or electroporation drug delivery catheters incorporating a plurality of internal electrodes are described in U.S. patent application Ser. No. 08/110,109 filed on Aug. 26, 1993, titled ENHANCED INTERNAL IONTOPHORESIS DRUG DELIVERY APPARATUS AND METHOD, and Ser. No. 08/129,252, filed on Sep. 29, 1993 titled ELECTROPORATION ENHANCED IN VIVO DRUG DELIVERY, both of which are hereby incorporated by reference for their disclosures relating to such devices.

Furthermore, although the catheters described above include balloons that function as drug delivery means, it will be understood that the concepts associated with multiple internal electrodes used for iontophoretic drug delivery can also be applied to those catheters that are designed for delivering drugs to body tissue without the need for expansion as provided by a balloon. In those devices, the drug delivery means may include permeable membranes, polymer matrix materials, and other drug delivery structures/materials as described herein. Such devices are disclosed in, for example, U.S. Pat. No. 5,286,254, which is entitled DRUG DELIVERY APPARATUS AND METHOD and U.S. patent application Ser. No. 07/973,263, filed on Nov. 9, 1992, entitled POLYMER MATRIX DRUG DELIVERY APPARATUS AND METHOD.

Figure 32:
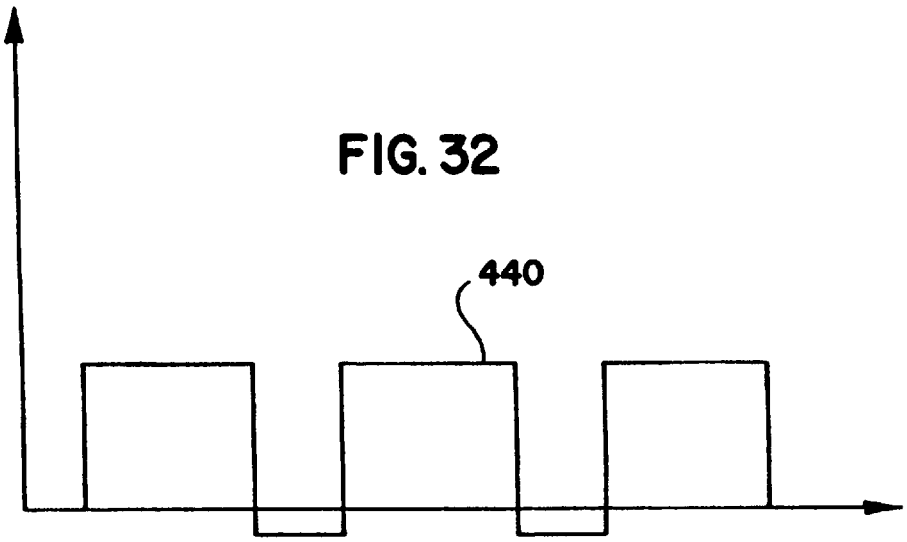
FIG. 32 is a depiction on one electric current/potential waveform useful with the apparatus and methods according to the present invention.

FIG. 32 is the graph of one waveform 440 that may also be useful for drug delivery with catheters according to the present invention. In particular, a waveform that reverses polarity may inhibit the formation of thrombus on positively charged electrode surfaces, as no one electrode is constantly positively charged. Although a rectangular waveform is depicted in FIG. 32, it will be understood that any waveform that reverses polarity would accomplish substantially the same result.

Additional variations in methods of suing the apparatus according to the present invention include providing the electric current/potential in waveforms having frequencies substantially higher than the intrinsic heart rate, preferably at 200 Hz or above most preferably from 2–15 kHz. Providing the electric current/potential at those higher frequencies further reduces the risk of inducing arrhythmias. The intensity level of the pulses can also be varied depending on the patients heart rate to provide higher intensity pulses during the safer portions of the heartbeat, i.e., the refractory period, and lower intensity pulses (or none at all), during the repolarization period during which the heart is most susceptible to induced arrhythmia. A more detailed discussion of the methods of providing such waveforms is found in commonly-assigned U.S. patent application Ser. No. 08/110,109, filed on Aug. 20, 1993, titled ENHANCED INTERNAL IONTOPHORESIS DRUG DELIVERY APPARATUS AND METHODS, which is incorporated by reference above. A discussion of the same considerations as they relate to electroporation-enhanced delivery can be found in U.S. patent application Ser. No. 08/129,252, filed on Sep. 29, 1993 titled ELECTROPORATION ENHANCED IN VIVO DRUG DELIVERY, which is also incorporated by reference above.

In addition to timing the delivery of high frequency pulses of electric current/potential to correspond with the patient's intrinsic heart rate, the apparatus and methods according to the present invention also can be used in conjunction with active pacing of the patient's cardiac activity. The electrodes used to provide the electric current/potential that enhances drug delivery also can be used to provide the pacing current or additional electrodes can be provided for pacing. A more detailed discussion of the use of active pacing in conjunction with active drug delivery as described in the present invention can be found in U.S. patent application Ser. No. 08/177,175, filed on Jan. 4, 1994 titled SIMULTANEOUS CARDIAC PACING AND LOCAL DRUG DELIVERY, which is hereby incorporated by reference.

Although the description of the preferred embodiments and methods have been quite specific, it is contemplated that various modifications could be made without deviating from the spirit of the present invention. Accordingly, it is intended that the scope of the present invention be dictated by the appended claims, rather than by the description of the preferred embodiments and methods.

The invention that we claim is:

1. An apparatus for delivering a drug to internal body tissue of a patient, the apparatus comprising:
   a catheter having an elongated body;
   a polymer matrix operably connected to and coaxially aligned with the elongated body, the polymer matrix being substantially non-compressible and configured to embody the drug, the polymer matrix selected from the group consisting essentially of polyethylene oxide, polyacrylamide, polyurethane rubber, and natural rubber; and
   transport means operably connected to the catheter, the transport means being configured to actively transport the drug from the polymer matrix to the internal body tissue.

2. The apparatus of claim 1 wherein the transport means comprises iontophoresis means.

3. The apparatus of claim 2 wherein the iontophoresis means comprises at least two electrodes configured to be placed in electrical communication with a power supply; at least one of the electrodes being positioned for electrical communication with the polymer matrix.

4. The apparatus of claim 3 wherein the plurality of electrodes comprises first and second electrodes, the first and second electrodes being operably connected to the catheter.

5. The apparatus of claim 1 wherein the catheter is flexible.

6. The apparatus of claim 1 wherein the elongated body has a circumference and the polymer matrix circumscribes the circumference.

7. An apparatus for delivering a drug to internal body tissue of a patient, the apparatus comprising:
   a catheter having an elongated body;
   a polymer matrix operably connected to the elongated body, the polymer matrix being substantially non-compressible and configured to embody the drug, the polymer matrix selected from the group consisting essentially of polyethylene polyetheline oxide, polyacrylamide, polyurethane rubber, and natural rubber;
   expansion means operably connected to the elongated body, the expansion means being configured to expand the polymer matrix in a direction substantially radial to the catheter; and
   transport means operably connected to the catheter, the transport means being configured to actively transport the drug from the polymer matrix to the internal body tissue.

8. The apparatus of claim 7 wherein the expansion means comprises a balloon.

9. An apparatus for delivering a drug to internal body tissue of a patient, the apparatus comprising:
   a catheter having a balloon;
   a polymer matrix operably connected to the balloon, the polymer matrix being substantially non-compressible and configured to embody the drug, the polymer matrix selected from the group consisting essentially of polyethylene oxide, polyacrylamide, polyurethane rubber, and natural rubber; and
   first and second electrodes configured to be placed in electrical communication to a power supply, the first electrode being positioned for electrical communication with the polymer matrix.

10. The apparatus of claim 9 wherein the second electrode is operatively connected to the catheter.

* * * * *